(12) United States Patent
Lemme et al.

(10) Patent No.: US 8,883,509 B2
(45) Date of Patent: Nov. 11, 2014

(54) APPARATUS AND METHOD FOR BIOLOGICAL SAMPLE PROCESSING

(75) Inventors: Charles D. Lemme, Tucson, AZ (US); William Richards, Tucson, AZ (US); Glen Ward, Tucson, AZ (US); Austin Ashby, Tucson, AZ (US); Andrew Ghusson, Tucson, AZ (US); Lisa Jensen-Long, Tucson, AZ (US); Kevin Knapp, Tucson, AZ (US); Rodney Kugizaki, Tucson, AZ (US); Alain Larson, Tucson, AZ (US); Paul Richards, Tucson, AZ (US); Wayne Showalter, Tucson, AZ (US); Chad Wilkinson, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 1217 days.

(21) Appl. No.: 12/167,459

(22) Filed: Jul. 3, 2008

(65) Prior Publication Data

US 2009/0017491 A1     Jan. 15, 2009

Related U.S. Application Data

(60) Provisional application No. 60/958,916, filed on Jul. 10, 2007.

(51) Int. Cl.
| | |
|---|---|
| *G01N 1/28* | (2006.01) |
| *G01N 35/02* | (2006.01) |
| *G01N 35/10* | (2006.01) |
| *G01N 35/00* | (2006.01) |
| *G01N 1/31* | (2006.01) |
| G01N 35/04 | (2006.01) |

(52) U.S. Cl.
CPC ...... *G01N 35/00029* (2013.01); *G01N 35/1011* (2013.01); *G01N 35/1002* (2013.01); *G01N 1/312* (2013.01); G01N 2035/0453 (2013.01); G01N 2035/00049 (2013.01); *G01N 35/0092* (2013.01); G01N 35/1081 (2013.01); G01N 2035/00138 (2013.01); G01N 2035/00376 (2013.01)
USPC ............... 436/46; 436/180; 422/64; 422/563; 422/536; 435/288.3

(58) Field of Classification Search
None
See application file for complete search history.

(56) References Cited

U.S. PATENT DOCUMENTS

| | | |
|---|---|---|
| 5,273,905 A | 12/1993 | Muller et al. |
| 5,314,825 A | 5/1994 | Weyrauch et al. |
| 5,595,707 A | 1/1997 | Copeland et al. |
| 5,650,327 A | 7/1997 | Copeland et al. |
| 5,654,199 A | 8/1997 | Copeland et al. |

(Continued)

FOREIGN PATENT DOCUMENTS

| | | |
|---|---|---|
| EP | 1 600 759 A2 | 11/2005 |
| WO | WO 91/13335 | 9/1991 |

(Continued)

*Primary Examiner* — P. Kathryn Wright
(74) *Attorney, Agent, or Firm* — Ventana Medical Systems, Inc.

(57) ABSTRACT

An apparatus and method are described that achieve independent and simultaneous processing of a plurality of substrate-supported biological samples. In one embodiment, substrate holders arranged in a minor arc are independently moveable between a processing position and an access position, and reagents are delivered to substrates held in the substrate holders through a nozzle plate that moves along the arc of substrate holders. The disclosed apparatus and method are particularly suited for implementation of lean processing of biological samples.

15 Claims, 22 Drawing Sheets

(56) References Cited

U.S. PATENT DOCUMENTS

| | | | |
|---|---|---|---|
| 5,654,200 A | 8/1997 | Copeland et al. | |
| 6,045,759 A | 4/2000 | Ford et al. | |
| 6,183,693 B1 | 2/2001 | Bogen et al. | |
| 6,192,945 B1 | 2/2001 | Ford et al. | |
| 6,296,809 B1 | 10/2001 | Richards et al. | |
| 6,405,609 B1 | 6/2002 | Richards et al. | |
| 6,416,713 B1 | 7/2002 | Ford et al. | |
| 6,534,008 B1 | 3/2003 | Angros | |
| 6,537,818 B2 | 3/2003 | Richards et al. | |
| 6,541,261 B1 | 4/2003 | Bogen et al. | |
| 6,544,798 B1 | 4/2003 | Christensen et al. | |
| 6,582,962 B1 | 6/2003 | Richards et al. | |
| 6,783,733 B2 | 8/2004 | Bogen et al. | |
| 6,855,292 B2 | 2/2005 | Angros | |
| 6,855,552 B2 | 2/2005 | Towne et al. | |
| 6,943,029 B2 | 9/2005 | Copeland et al. | |
| 6,945,128 B2 | 9/2005 | Ford et al. | |
| 7,067,325 B2 | 6/2006 | Christensen et al. | |
| 7,217,392 B2 | 5/2007 | Bogen et al. | |
| 7,220,589 B2 | 5/2007 | Richards et al. | |
| 7,250,301 B2 | 7/2007 | Angros | |
| 7,400,983 B2 | 7/2008 | Feingold et al. | |
| 7,470,541 B2 | 12/2008 | Copeland et al. | |
| 7,476,362 B2 | 1/2009 | Angros | |
| 2002/0116132 A1 | 8/2002 | Rhett et al. | |
| 2003/0138353 A1 | 7/2003 | Bargoot et al. | |
| 2004/0014222 A1 | 1/2004 | Towne et al. | |
| 2004/0191128 A1* | 9/2004 | Bogen et al. | 422/100 |
| 2005/0035156 A1* | 2/2005 | Hersch et al. | 222/504 |
| 2005/0159982 A1 | 7/2005 | Showalter et al. | |
| 2006/0019302 A1 | 1/2006 | Lemme et al. | |
| 2006/0093520 A1* | 5/2006 | Lemme et al. | 422/64 |
| 2006/0105359 A1* | 5/2006 | Favuzzi et al. | 435/6 |
| 2006/0275861 A1 | 12/2006 | Angros et al. | |
| 2006/0275889 A1 | 12/2006 | Angros et al. | |
| 2006/0281116 A1 | 12/2006 | Angros et al. | |
| 2007/0141711 A1 | 6/2007 | Stephens et al. | |
| 2008/0235055 A1 | 9/2008 | Mattingly et al. | |
| 2008/0318305 A1 | 12/2008 | Angros | |
| 2013/0071858 A1* | 3/2013 | Bui et al. | 435/7.21 |

FOREIGN PATENT DOCUMENTS

| | | |
|---|---|---|
| WO | WO 93/20440 | 10/1993 |
| WO | WO 9411720 A1 * | 5/1994 |
| WO | 99-44032 | 9/1999 |
| WO | WO 03/091710 A1 | 11/2003 |
| WO | 2004-001390 | 12/2003 |

* cited by examiner

APPARATUS AND METHOD FOR BIOLOGICAL SAMPLE PROCESSING

RELATED APPLICATION DATA

This claims the benefit of U.S. Provisional Patent Application No. 60/958,916, filed Jul. 10, 2007, which application is incorporated by reference herein.

BACKGROUND OF THE INVENTION

1. Field

The present invention relates to equipment and methods for preparing samples for analysis. In particular, the invention relates to equipment and methods for automated processing of biological samples on substrates.

2. Background

Primary staining, special staining, immunochemical analyses, and in situ hybridization (ISH) analyses are utilized to analyze a variety of biological samples including microarray samples, tissue samples and tissue array samples. These techniques are inherently inconsistent when performed manually, especially by multiple different persons. Inconsistent staining makes it difficult for a pathologist or other medical or research personnel to interpret samples and to make comparisons between different samples. Thus, a number of devices and methods have been described that serve to automate the staining process and reduce staining inconsistency. Labor costs and the burgeoning demand for anatomical pathology services for both the clinical and research markets also are driving the push for increased automation of the sample treatment process.

In concert with automation, laboratory work-flow improvements (see, for example, U.S. patent application Ser. No. 11/639,586, which is incorporated by reference herein) can decrease sample turn-around time. However, constraints imposed by currently available sample processors, and in particular batch sample processors, reduce the extent to which such "lean" methods can increase workflow.

SUMMARY

A biological sample processing apparatus is disclosed. In one embodiment, the apparatus includes a plurality of substrate holders where each substrate holder is automatically and independently movable between a different processing position and a different access position, and a moveable sample processor configured to simultaneously process two or more substrates held on two or more substrate holders in their different processing positions. In particular embodiments, the apparatus is configured to independently process each of a plurality of samples in a manner that permits samples to be individually added or retrieved from the system without interrupting the processing of other samples in the apparatus. A particular advantage of the disclosed system is its compatibility with lean work-flow methods for sample processing, such as pacing sample processing with sample preparation.

DETAILED DESCRIPTION OF SEVERAL ILLUSTRATIVE EMBODIMENTS

Figure 1:
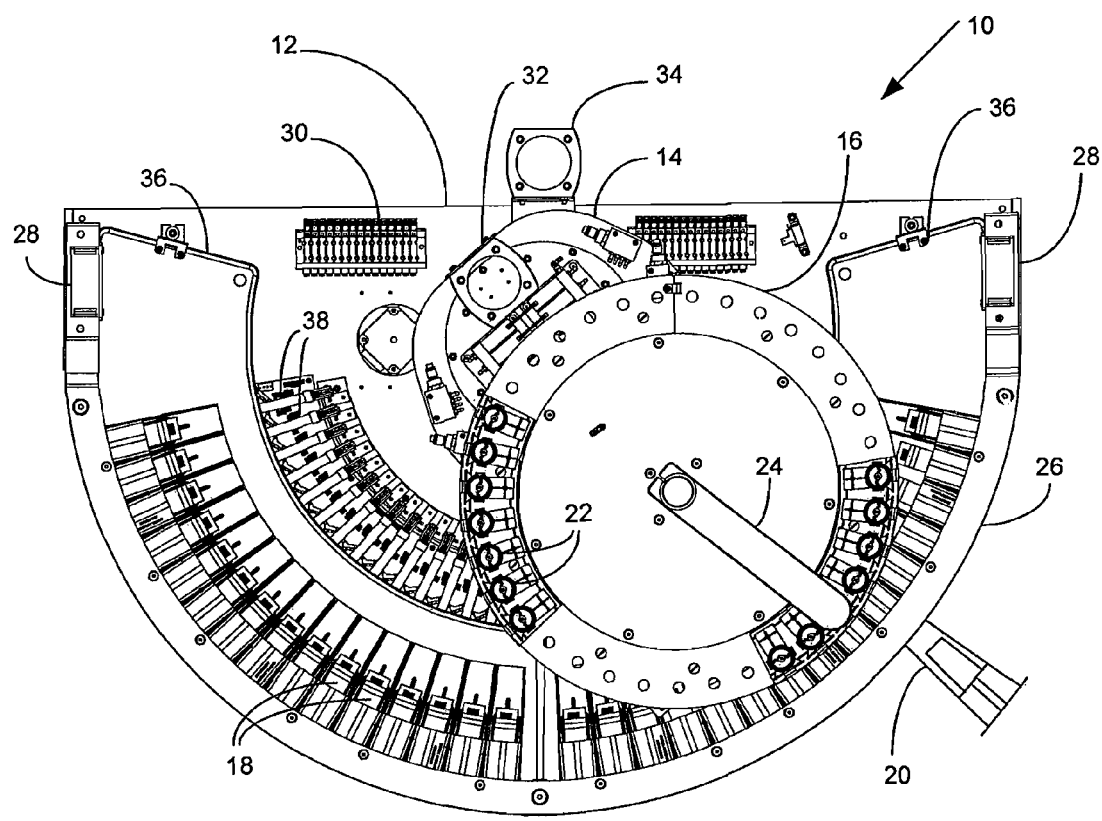
FIG. 1 is a top view diagram of an embodiment of a disclosed substrate processing portion of an automated substrate processing apparatus.

The following description of several embodiments describes non-limiting examples that further illustrate the invention. All titles of sections contained herein, including those appearing above, are not to be construed as limitations on the invention, but rather they are provided to structure the illustrative description of the invention that is provided by the specification. Also, in order to aid the reader in understanding the various illustrated embodiments, explanations of d terms are provided after an overview of embodiments of the invention.

I. Overview

In one embodiment, an automated biological sample processing apparatus is disclosed that includes a plurality of substrate holders where each substrate holder is automatically and independently movable between a different processing position and a different access position. For example, the processing position can be a position within the apparatus where a biological sample is processed, and the access position can be a position where a user can place a substrate-supported sample on a substrate holder without interfering with the processing of other samples in the apparatus. The apparatus also includes a movable substrate processor configured to simultaneously process two or more substrates held on two or more substrate holders in their different processing positions, for example, two or more substrates on adjacent substrate holders. The apparatus can further be operated in a manner that permits user access to replenish reagents needed for sample processing with minimal disruption of the processing of samples, and also in which user access is available to samples that have completed processing prior to completion of processing of other samples. Furthermore, processing of additional, individual samples can be started while other samples are already being treated by the apparatus. All of these features, and others described herein, provide laboratory personnel the flexibility to improve workflow in view of inconsistent levels of sample processing needs over time.

The disclosed apparatus can include a plurality of substrate holders that include independent thermal control units that permit independent temperature programming of each of the plurality of substrate holders, and hence the samples held on substrates placed thereon. In one embodiment, the independent thermal control units include conductive heating platforms where the substrate is heated by direct contact with a heated surface. In another embodiment, the independent thermal control units include radiant heating platforms where the substrate is heated radiantly and possibly convectively through an air gap above a heated surface that emits infrared radiation. In yet another embodiment, the independent thermal control units include heating and cooling platforms such Peltier devices. Of course, any combination of conductive heating, radiant heating, and heating and cooling platforms can be included on the plurality of substrate holders.

In a particular embodiment, the disclosed apparatus includes a non-contact temperature sensor positioned to measure a temperature of at least one of an upper surface of a substrate, a biological sample on the upper surface of the substrate, and a volume of liquid covering at least a portion of the upper surface of the substrate. In a more particular embodiment, the non-contact temperature sensor is connected in a feedback loop with a power supply for the thermal control unit so that the unit can maintain a substrate sample or liquid at a pre-determined temperature.

In other particular embodiments, the independent thermal control units comprise a source of air flow past one or more of the substrate holders, for example, each of the plurality of substrate holders can have a separate source of air flow, and the air flow past each of the substrate holders can be separated. In a more particular embodiment, the air flow past each of the substrate holders is directed toward a common point at a distance beyond the substrate holders.

In another embodiment of the disclosed apparatus, the plurality of substrate holders in their different processing positions are arranged in substantially the same plane and substantially along a minor arc (a portion of a circle of less than 180 degrees) having a minor arc radius, and the substrate processor is rotatably mounted (such as on a bearing) at a center of the minor arc and moves along a path parallel to and in a plane above the minor arc. In a particular embodiment, the substrate processor can be an elongate nozzle plate having a first end at which it is mounted and a second end, where the second end is located along a length of the nozzle plate toward the minor arc of the substrate holders. At the second end of the nozzle plate can be located a plurality of nozzles arranged in a plate arc, the plate arc having substantially the same radius as the minor arc along which the substrate holders are arranged. In a more particular embodiment, the plate arc of nozzles is smaller in length than the minor arc along which the substrate holders are arranged. Nozzles mounted on the second end of the nozzle plate can include two or more of a vortex mixing nozzle, a bulk reagent dispense nozzle, a jet-drain nozzle, and a rinse nozzle (see, for example, U.S. Pat. No. 6,943,029, which is incorporated by reference herein), and a railed aspirator as is discussed in Example 3 that follows.

In another particular embodiment, a nozzle plate can further include a reagent carousel rotatably mounted on the nozzle plate. And, for example, a plurality of dispensers can be arranged around the circular profile of a cylindrical reagent carousel mounted with its axis perpendicular to the nozzle plate (see, for example, U.S. Pat. Nos. 6,943,029; 6,945,128; 6,416,713; 6,192,945; and, 6,045,759; each of which patents are incorporated by reference herein).

In another embodiment, the apparatus further includes an enclosure housing the substrate holders in the different processing positions, from which enclosure the substrate holders are extended outside of the enclosure to different access positions. In yet another embodiment, processing of biological samples held on one or more substrate holders in different processing positions automatically continues while one or more of the sample holders are in different access positions.

In still another particular embodiment, an automated biological sample processing apparatus is disclosed that includes a plurality of substrate holders arranged in substantially the same plane along a minor arc of a circle, the circle having a first radius. An elongate nozzle plate is rotatably mounted at the center of the circle and extends toward the minor arc, but in a plane above the plurality of substrate holders, and along a radial line of the minor arc. A cylindrical reagent dispenser carousel is rotatably mounted on the elongate nozzle plate, the cylindrical carousel having an axis and a second radius, the second radius being smaller than the first radius. The cylindrical carousel is mounted on the elongate nozzle plate such that a reagent dispenser on the carousel can be positioned over a substrate holder along the minor arc through a combination of rotational movement of the nozzle plate around the center of the circle and rotational movement of the carousel around its axis. In a more particular embodiment, each of the plurality of substrate holders is independently extendable outward from the minor arc along separate radial lines of the minor arc to a second minor arc. In another more particular embodiment, ambient air is directed along radial lines of the minor arc past two or more of the substrate holders, and even more particularly the ambient air can be directed past the substrate holders toward the center of the circle of which the minor arc is part. Ambient air directed past a first substrate holder can be substantially separated from ambient air directed past a second substrate holder.

In another aspect, a method is disclosed for continuous-access processing of a plurality of substrate-supported biological samples in an automated biological processing apparatus, where the apparatus has a plurality of separate substrate support units that are each automatically and independently movable between a separate processing position and a separate access position. In one embodiment, the method includes placing a substrate-supported sample onto a substrate support unit in an access position, automatically moving the substrate support unit to a processing position in response to a user command, automatically detecting the substrate-supported sample moved into the processing position on the substrate support unit, and initiating processing of the detected sample in a pre-determined order of steps. The pre-determined order of steps can be carried out independently of processing steps in progress on other samples already being processed by the apparatus, and independently of processing steps initiated for additional samples later added to the system.

In a particular embodiment, the method includes automatically alerting a user when processing of a sample is completed. In another particular embodiment, a sample is a member of a pre-selected grouping of samples and the method further includes automatically alerting a user when processing of the samples in the pre-selected grouping of samples is completed. Pre-selected groupings of samples can include two or more of a sample treated with a histochemical stain, a sample treated with an immunochemical reagent, and a sample treated with an in situ hybridization reagent. Examples of pre-selected groupings include two or more samples obtained from the same subject or patient, and two or more samples ordered by a single medical professional such as a pathologist reviewing a particular patient's case.

In one particular embodiment, the user command that initiates movement of a sample holder from the access position to the processing position comprises a touch command executed through a sensor located on an exterior portion of the substrate-support unit. A user can also be prompted to input a command causing a completed sample to be moved, on a substrate support unit, into the access position for retrieval of the completed sample from the apparatus. The command causing the completed sample to be moved to the access position for retrieval also can be a touch command executed through a sensor located on an exterior portion of the substrate support unit. In a more particular embodiment, the separate processing position and the separate access position of each of the plurality of substrate support units lie along different radial lines of a minor arc of a circle.

In another embodiment of the method, the step of initiating processing of the sample in the pre-determined order of steps comprises initiating processing according to an order of steps encoded by a machine-readable code associated with the substrate-supported sample.

In yet another embodiment, the method can include "landing zones," which are points in time calculated to provide a coordinated pause of all samples currently being processed in a state where they can safely remain (e.g. without drying or extended exposure to reagents that should be removed within a certain time frame) such that a user can access reagent containers within the instrument and either replenish the reagents or change the reagents. Such landing zones are advantageous for providing points in time (which can be indicated by an alarm to alert laboratory personnel) when reagents needed for the performance of particular tests on newly added samples can be added with minimal disruption of processing of samples that are already being processed at the time the landing zone is established.

Also disclosed is a method for improving the coordination of biological sample processing with biological sample preparation. The method includes cutting a tissue section (such as a formalin-fixed paraffin-embedded tissue sample, a fresh frozen tissue sample, or a tissue array sample); placing the tissue section on a substrate, the substrate including a machine-readable code that specifies a pre-determined set of sample processing steps for the tissue section; placing the tissue section on the substrate into an unoccupied substrate support unit of a biological sample processing apparatus, the apparatus having a plurality of separate substrate support units where each of the substrate support units are automatically and independently movable between a separate processing position and a separate access position, the unoccupied substrate support unit held in the access position to receive the substrate; causing the substrate support unit to move to the processing position; and initiating processing of the sample without interrupting the processing of other samples already being processed by the apparatus. The method can further include alerting a user that a substrate support unit of the apparatus is unoccupied and ready to receive a substrate supporting a tissue sample, or alerting the user that a substrate supporting a tissue sample for which processing is completed can be retrieved from the apparatus to provide the unoccupied substrate support unit.

Also disclosed are a method, system and program storage device for controlling the operation of a biological sample treatment system that provides opportunities to replenish or change reagents on the system, particularly where each of a plurality of samples is independently being processed by the system. The method includes determining pause point steps for each sample of the plurality of samples; calculating a landing zone by aligning the pause points for all of the plurality of samples; and, automatically stopping processing of samples at the landing zone and automatically providing access to a plurality of reagent containers held on the system so that the reagent containers can be changed.

These and other aspects of the disclosure will become more apparent through the discussion of terms and the Examples that follow.

II. Terms

Unless defined otherwise, all technical and scientific terms used herein have the same meanings as commonly understood by one skilled in the art to which the disclosed invention pertains.

The singular forms "a," "an," and "the" include plural referents unless the context clearly indicates otherwise. Thus, for example, reference to "a reagent" refers to one or more reagents, such as 2 or more reagents, 3 or more reagents, or 4 or more reagents.

The term "biological sample" refers to any sample including a biomolecule (such as a protein, a peptide, a nucleic acids, a lipid, a carbohydrate or a combination thereof) that is obtained from or includes any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (for example, cytological smears such as Pap or blood smears or samples of cells obtained by microdissection), samples of whole organisms (such as samples of yeast or bacteria), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, milk, vaginal fluid, saliva, swabs (such as buccal swabs), or any material containing biomolecules that is derived from a first biological sample.

The term "machine-readable code" refers to any type of optical symbology, magnetic pattern or electromagnetic or electrostatic signal having information content. For example, information content relating to sample identity, sample origin, sample chain of custody, instructions for processing a sample, information regarding the characteristics of a sample, test results for a sample, images of the sample and the like. A "code reader" is any type of machine that can decipher, translate or interpret the information contained in a machine-readable code, for example, a device that converts the code into commands for performing an automated procedure or presenting the information in a human-readable or human-interpretable form. A code reader can be compatible with one or more different types of machine-readable code. Examples of optical symbologies include characters, barcodes and dataglyphs. Particular examples of barcodes include linear barcodes (such as EAN.UPC, EAN-128, ITF-14 and code 39) multi-dimensional barcodes such as 2D stacked symbologies and 2D matrix symbologies, and composite barcodes such as reduced-space symbologies. Even more particular examples of 2D optical symbologies include (p, q) code, PDF417, data matrix, maxicode, vericode, codablock, aztec code, code 16K and QR code. Bar code readers for these and any number of other optical symbologies are well known. Where the machine-readable code comprises characters (such as alphanumeric characters such as English text and Arabic numbers) the code reader can be an optical character reader (OCR). Magnetic stripes are only one example of a device that can store information in the form of a magnetic pattern. An example of an electromagnetic code is an RFID tag. RFID tags typically include a small metallic antenna and a silicon chip, and can be active or passive. RFID code readers are well known, and typically include an antenna and a transceiver that receives information from the RFID tag. The information content of an RFID tag can be fixed or changeable. In another embodiment, the code reader comprises a CCD camera and the CCD camera can be used for simultaneous detection of samples and reading of a barcode or characters. Other examples of machine-readable codes that can be used include Bragg-diffraction gratings and micro- or nano-barcodes (such as spatial and spectral patterns of fluorescent particles or spatial patterns of magnetic particles).

A "plurality" refers to two or more, for example, 3 or more, 4 or more, 5 or more, 10 or more, or even 20 or more.

As used herein, the term "reagent" refers to any liquid or liquid composition used in a sample processing operation that involves adding a liquid or liquid composition to a sample. Reagents include solutions, emulsions, suspensions and solvents (either pure or mixtures thereof). Reagents can be aqueous or non-aqueous. Examples of reagents include solutions or suspensions of antibodies, solutions or suspensions of nucleic acid probes, and solutions or suspensions of dye or stain molecules (such as H&E staining solutions and Pap staining solutions). Further examples of reagents include solvents and/or solutions for de-paraffinization of paraffin-embedded biological samples such as limonene, aqueous detergent solutions, and hydrocarbons (for example, alkanes, isoalkanes and aromatic compounds such as xylene). Additional examples of reagents include solvents (and mixtures thereof) that can be used to dehydrate or re-hydrate biological samples, such as ethanol, water and mixtures thereof.

The term "substrate" refers to any substrate (such as glass, quartz, plastic or silicon) of any dimensions on which a biological sample is placed for analysis, and more particularly to a "microscope slide" such as a standard 3"×1" glass slide or a standard 75 mm×25 mm glass slide. Examples of biological samples that can be placed on a substrate include a cytological smear, a thin tissue section (such as from a biopsy), or alternatively, the sample can be an array of biological samples, for example, a tissue array, a DNA array, an RNA array, a protein array, or any combination thereof. Thus, in one embodiment, tissue sections, DNA samples, RNA samples, and/or proteins are placed on a substrate at particular locations. Additional examples of substrates include substrates used to assist in analysis of a sample such as SELDI and MALDI chips.

The term "substrate processing operation" refers to any treatment or manipulation of a substrate such as a microscope slide, either with or without a biological sample already placed thereon, or any treatment of a biological sample placed on a substrate. Examples of substrate processing operations include, but are not limited to, cleaning, heating, cooling, drying, baking, labeling, indexing, removing mercury deposits, re-hydrating, dehydrating, fixing, de-paraffinizing, decalcifying, bluing, digesting, preserving, pre-stain prepping, solvent exchanging, mounting, staining and coverslipping, and combinations thereof.

The term "staining" is used herein to refer to any treatment of a biological sample (such as a cellular smear or a tissue section) that detects and/or differentiates the presence, location and/or amount (such as concentration) of a particular molecule (such as a lipid, protein or nucleic acid) or particular structure (such as a normal or malignant cell, cytosol, nucleus, Golgi apparatus, or cytoskeleton) in the biological sample. For example, staining can provide contrast between a particular molecule or a particular cellular structure and surrounding portions of a biological sample, and the intensity of the staining can provide a measure of the amount of a particular molecule in the sample. Staining can be used to aid in the viewing of molecules, cellular structures and organisms not only with bright-field microscopes, but also with other viewing tools such as phase contrast microscopes, electron microscopes and fluorescence microscopes. Some staining methods can be used to visualize an outline of a cell. Other staining methods rely on certain cell components (such as molecules or structures) being stained without staining the rest of a cell. Examples of types of staining methods include histochemical methods, immunohistochemical methods and other methods based on reactions between molecules (including non-covalent binding interactions), for example, hybridization reactions between nucleic acid molecules. Particular staining methods include, but are not limited to, primary staining methods such as hematoxylin & eosin (H&E) staining and Pap staining, enzyme-linked immunohistochemical methods and in situ RNA and DNA hybridization methods such as fluorescence in situ hydbridization (FISH), chromogenic in situ hybridization (CISH), and silver in situ hybridization (SISH) methods. Additional particular examples of staining methods can be found, for example, in Horobin and Kiernan, "Conn's biological stains: a handbook of dyes, stains and fluorochromes for use in biology and medicine," $10^{th}$ ed., Oxford: BIOS, ISBN 1859960995, 2002, and in Beesley, "Immunocytochemistry and in situ hybridization in the biomedical sciences," Boston: Birkhauser, ISBN 3764340657, 2002.

III. Examples

Example 1

Biological Sample Processing Unit

Various prior staining instruments have been of a batch architecture, where a batch of microscope slides is processed together. The batch size can vary but all slides in a batch are processed as a group, and more particularly as a group having common processing steps that are shared amongst the batch of slides. A batch instrument has several disadvantages relating to how it disrupts the flow of work through a laboratory. For example, the instrument cannot be started until a full batch of similar slides become available, otherwise to run less than a full batch sacrifices the instrument's capacity. This means that slides that are ready to be stained early in the day must wait until there are enough slides available to make the run efficient, delaying patient results that are so important when a patient has learned they may have a serious medical condition. Another disadvantage of batching results from the fact that the time to finish different processing protocols varies significantly. For example, a simple IHC protocol might be finished in less than two hours, while a more complicated ISH protocol could take five or more hours. When run together as a batch, the samples subjected to the shorter protocol that are done earlier are held hostage to the slower protocols that finish at a later time. None of the samples finished more quickly can be removed from the instrument until the longest protocol is complete, and to do so is difficult without interrupting and possibly compromising the integrity of the results for the longer protocols. Still a further deficiency of batch instruments is that samples originating from the same patient or same ordering healthcare professional tend to become shuffled amongst several batches such that they must be manually sorted after removal from the instrument.

The particular embodiment of the disclosed apparatus described in this Example overcomes the shortcomings of prior batch instruments. In this embodiment, each substrate (such as a microscope slide) position in the apparatus is its own staining platform, totally independent of the other positions. The configuration permits addition of a new substrate whenever a processing position becomes available, regardless of the state of other substrates being processed in other positions. And, furthermore, the configuration permits a user to remove a processed sample as soon as it is completed. In a particular embodiment, substrate-supported samples can be automatically sorted during removal from the apparatus according to any pre-selected grouping. For example, substrates can be grouped according to any typed of information that is associated with the substrate, such as according to patient, pathologist, clinic, type of stain, etc. In addition to providing these enhanced work-flow attributes, the apparatus described in this example can perform multiple IHC protocols and multiple ISH, in any combination, and in any order, without increasing the time such protocols would otherwise take in a batch dedicated to a single such protocol.

Making each substrate position into its own independent treatment platform is accomplished in the embodiment of this Example through independent substrate holders, each substrate holder being part of a staining "cell," each cell accommodating a single substrate. Each cell is independent of the other cells both thermally and fluidically. Specifically, each substrate can be controlled to whatever temperature is needed to accomplish a particular substrate processing step and is treated with whatever reagents are necessary in a particular processing step, and is rinsed as necessary without regard to the temperature, fluids or rinsing state of the other substrates. Each cell can be loaded or unloaded according to the needs of its processing schedule without influencing the state of other cells. This is accomplished in the apparatus of this Example with a heater platform on which a substrate is processed that is moveable from a processing position to an access position, and in particular a heater platform on a linear slide combined with a means to move the heater platform away from a processing position in proximity to a substrate processor to an access position where the heater platform is accessible to an operator for loading or unloading of substrates onto or off of the heater platform.

The cells can be arranged in any geometrical pattern that permits a substrate on a substrate holder (such as a heater platform) to be located in proximity to various devices used during substrate processing steps (such as a nozzle, a bar code reader or other code reader, a sample sensor, and a reagent dispenser) in the processing position and moved away from such devices in the access position. In this embodiment, the various substrate processing devices are attached to a nozzle plate that sequentially moves from one cell to the next, bringing the various devices to each cell in turn, and more particularly bringing two or more different devices to two or more cells simultaneously.

One possible arrangement is to align the cells adjacent to each other in a linear fashion and move the nozzle plate on a linear drive so that the devices on the nozzle plate are sequentially moved past each cell and utilized as necessary to carry out a pre-determined sequence of substrate processing steps on substrates being treated in a particular cell. When the last device along the nozzle plate that is needed to perform a pre-determined processing step is at the furthest-most substrate for which a processing step is due, the nozzle plate rapidly returns to the other end and repeats the traverse past the cells to the extent necessary. Bulk fluid reagents (such as wash, deparaffinization, and cell-conditioning reagents common to a plurality of protocols) and air are plumbed to nozzles on the nozzle plate and particular reagents (such as particular antibodies, particular nucleic acid probes, and particular detection chemicals) are dispensed from a reagent carousel that is attached to the nozzle plate and rotates above the samples. Alternatively, reagents can be dispensed using a syringe pump system that is attached to the nozzle plate. A disadvantage of this geometry is the rather long length of the instrument, which can be an issue in a small laboratory space.

An arrangement that accomplishes the same function, while using less floor space is now described with reference to the figures. As shown in FIG. 1 in top view, each "cell" 18 in a processing position of substrate processing assembly 10 functions as a substrate holder that is movable to an access position 20, and in the illustrated embodiment each cell 18 is shaped as a small segment of an annulus, about 5° in extent. The cells 18 are arranged in an arc that has an outer radius of about 21 inches so that thirty cells take up about 155° of arc (outside to outside of the segments) and the instrument is about 42 inches wide and 30 inches deep. With the cells arranged in an arcuate shape, the nozzle plate 14 rotates from the center of the arc of cells, so that its outer edge, on which a variety of substrate processing devices are attached, remains at a constant radial distance from the center of the arc, and located over the cells.

The substrate processing assembly 10 show in top view in FIG. 1 also includes base plate 12 (which can be made, for example, of 0.625" thick aluminum tooling plate, such as MIC-6) through which nozzle plate 14 is rotatably mounted. Reagent carousel 16 is rotatably mounted on nozzle plate 14, and includes a plurality of reagent dispensers 22 and dispenser hammer arm 24. Around the arc of the substrate processing assembly 10 is gas conduit 26 connected to blowers 28 for supplying ambient air that can be flowed past each substrate holder in certain embodiments. Valving 30 provides independent sources of compressed air to air cylinders 38, and the compressed air is used to move cells 18 in their processing positions to their access position 20, and then back to the processing position. Also shown in FIG. 1 are fluidic conduit connections 32 and 34 that are used to hold a flexible conduit through which fluids (and also compressed air and/or vacuum) can be supplied to the nozzles (not shown) on nozzle plate 14 from a fluidics supply module (not shown). A pan 36 extends around the arc of the substrate holders underneath the cells 18 to catch waste fluids that are directed to a waste capture module (not shown).

Figure 2:
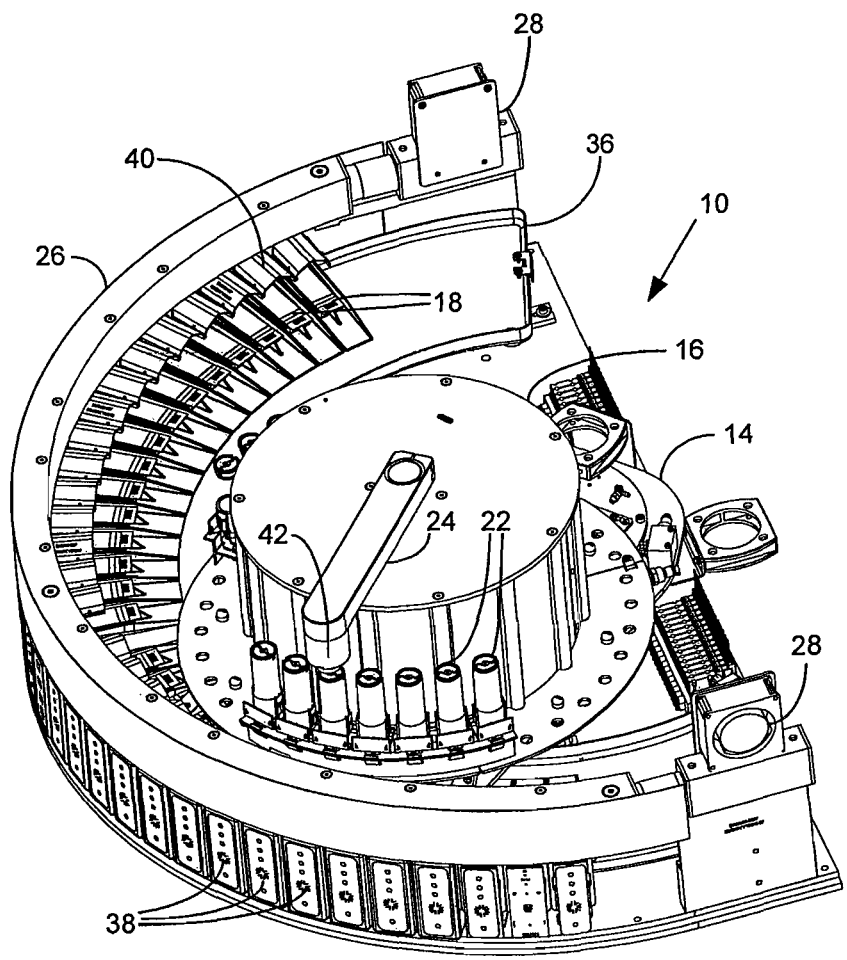
FIG. 2 is a perspective view diagram of an embodiment of a disclosed substrate processing portion of an automated substrate processing apparatus viewed from above.

FIG. 2 provides a perspective view of the substrate processing assembly 10 that illustrates many of the features of FIG. 1 (having the same reference numbers), but also provides a view of an exterior portion 38 of the cells 18 that can include a plurality of different indicator lights (such as different colored LED lights) and a touch sensor for activating movement of a cell from a processing position to an access position, or vice versa. Also shown in FIG. 2 is splash guard 40 that helps prevent a reagent applied to a substrate in one cell from splashing into an adjacent cell. Dispenser hammer 42 operates to depress the dispensers 22 and eject a reagent onto a substrate when a dispenser is located under dispenser hammer arm 24.

Figure 3:
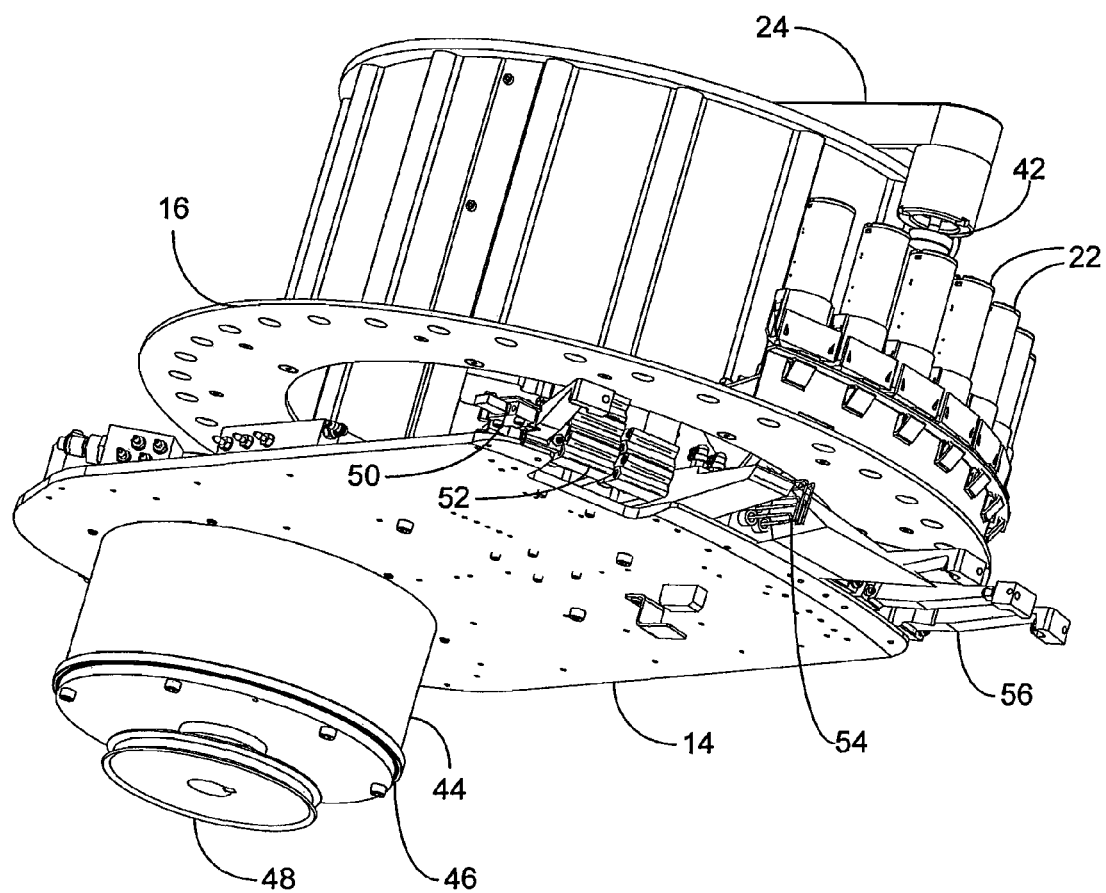
FIG. 3 is a perspective view diagram of an embodiment of a disclosed substrate processing portion of an automated substrate processing apparatus viewed from below.

FIG. 3 provides an underside perspective view of the nozzle plate 14 and reagent carousel 16 rotatably mounted to the nozzle plate. In addition to features discussed in regard to FIGS. 1 and 2, FIG. 3 also shows pivot 44 of nozzle plate 14, a bearing 46 that supports the nozzle plate in the apparatus, and pulley 48 that is used to transfer torque that rotates nozzle plate 14 past the substrate processing cells arranged in an arc on the upper surface of the substrate processing assembly 10. FIG. 3 also illustrates the elongate shape of nozzle plate 14 having at one end the pivot 44 around which it rotates and a second end bearing a plurality of nozzles and other devices, which include in this embodiment a substrate detection sensor 50, a pair of stacked dual rinse nozzles 52 (which can be raised and lowered to provide alternative sets of rinsing jets), a set of dispense nozzles 54, and a vortex mixing nozzle 56.

Figure 4:
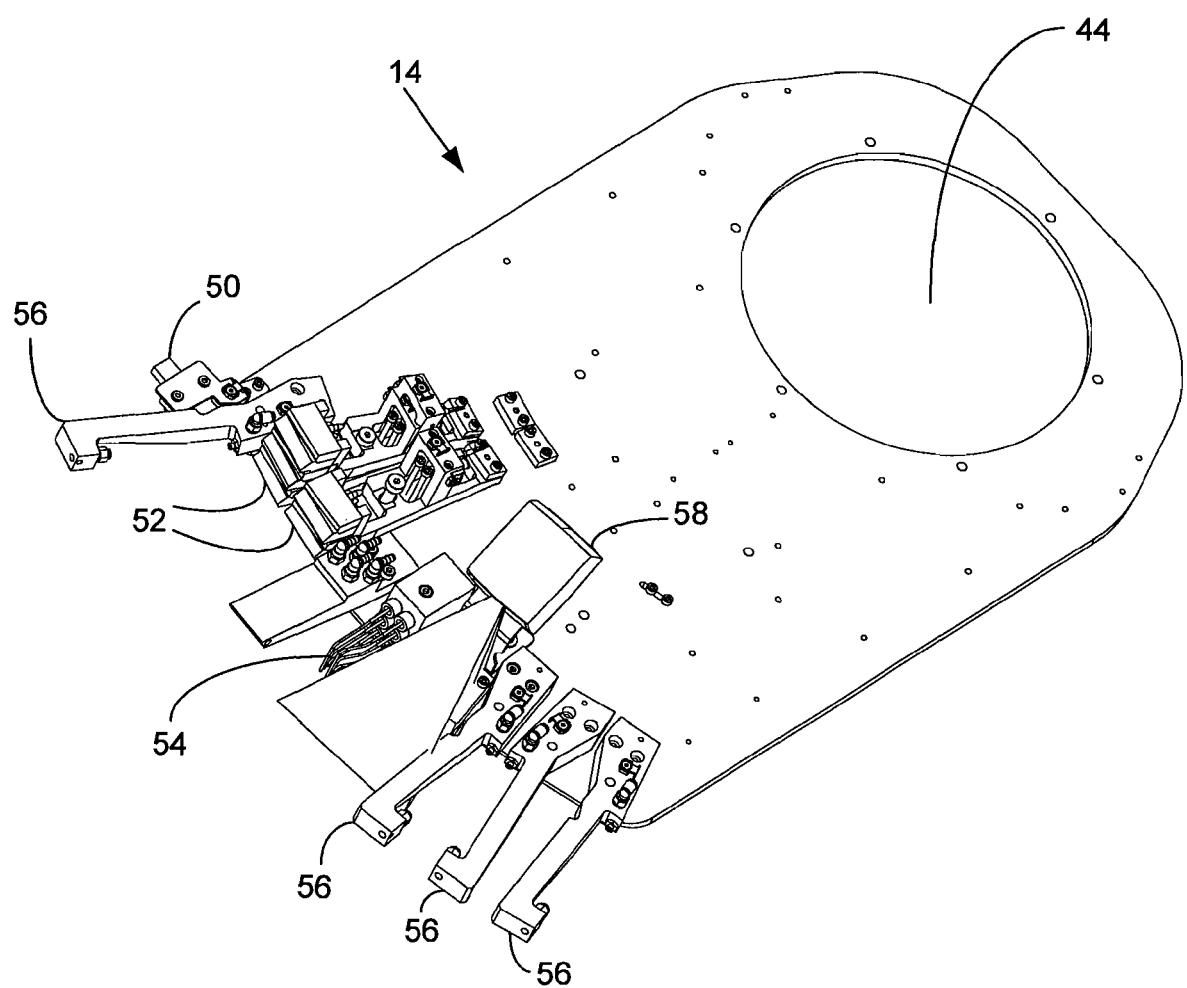
FIG. 4 is a perspective view diagram of an embodiment of a nozzle plate including a variety of nozzles positioned along a plate arc.

FIG. 4 shows a perspective view of nozzle plate 14 from above with the reagent carousel removed and showing pivot 44 around which the nozzle plate is rotated. Attached to the nozzle plate at the second end, which second end has an arc of shorter length but the same radius as the arc in which the cells of the apparatus are arranged, are a plurality of nozzles and devices that are moved past the substrates held in their substrate holders. Included in this plurality of nozzles and devices are substrate detection sensor 50, a pair of stacked dual rinse nozzles 52, a set of six reagent dispense nozzles 54, four vortex mixing nozzles 56, and a code reader 58. An additional unlabeled nozzle is shown between a dual rinse nozzle 52 and dispense nozzles 54, for a total of 9 devices or nozzles that can be passed over substrates and used as needed to accomplish scheduled substrate processing operations. In one embodiment, two or more substrates are simultaneously processed using two or more of the devices/nozzles on the nozzle plate. Additional devices and types of nozzles can be added to a nozzle plate, or substituted for those shown (for example a railed aspirator as discussed in Example 3 or a radiant heater that can be used to bake a sample onto a substrate).

Figure 5:
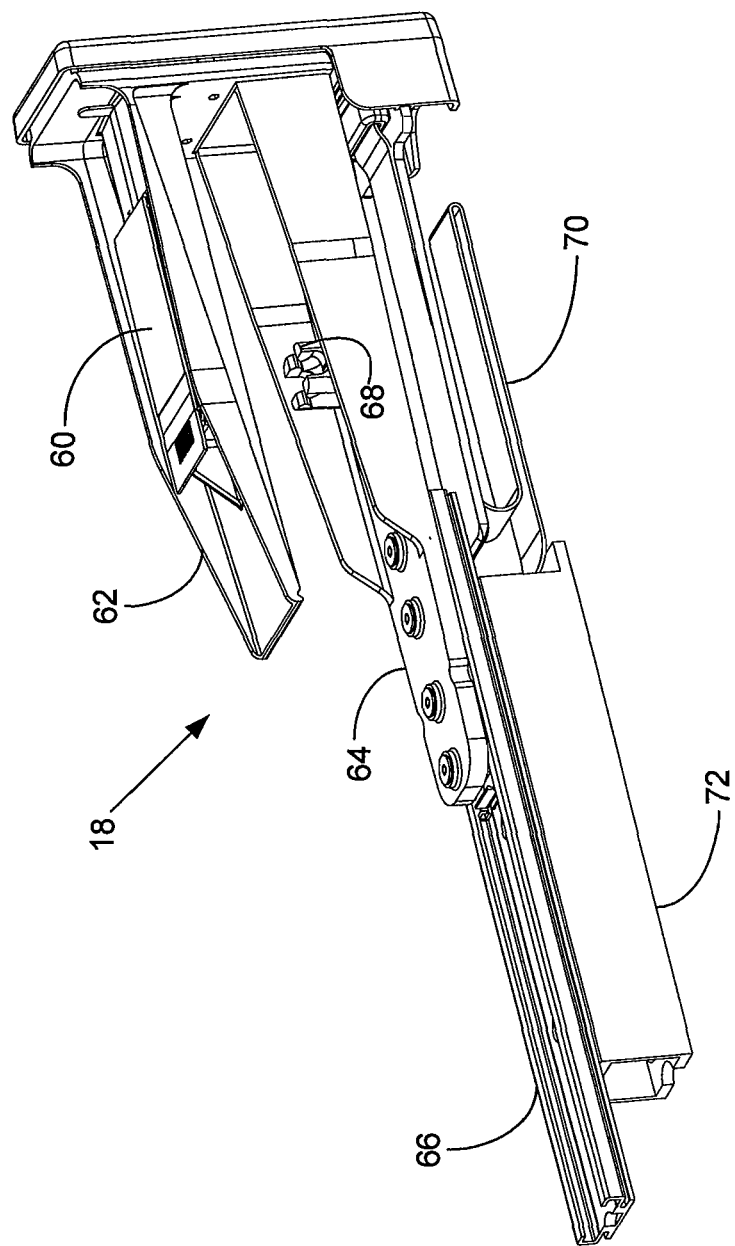
FIG. 5 is a perspective view diagram of an embodiment of a substrate holder mounted on a sample rail to permit movement between a processing position and an access position.

FIG. 5 shows a single cell 18 in perspective view. In this embodiment a microscope slide 60 having a barcode at one end is held on heater platform 62. The assembly 64 is slideably attached to slide 66. Attachment point 68 is where an air cylinder can be attached, which air cylinder can be used to move the cell from a processing position to an access position. Slide 66 is attached to base 72 that houses flex cable 70 when the cell is in a processing position and from which the flex cable unfurls as the cell is moved to an access position (as shown). The flex cable 70 provides electrical connection to the heater platform 62 and other electronic devices that are part of the movable cell.

Figure 6:
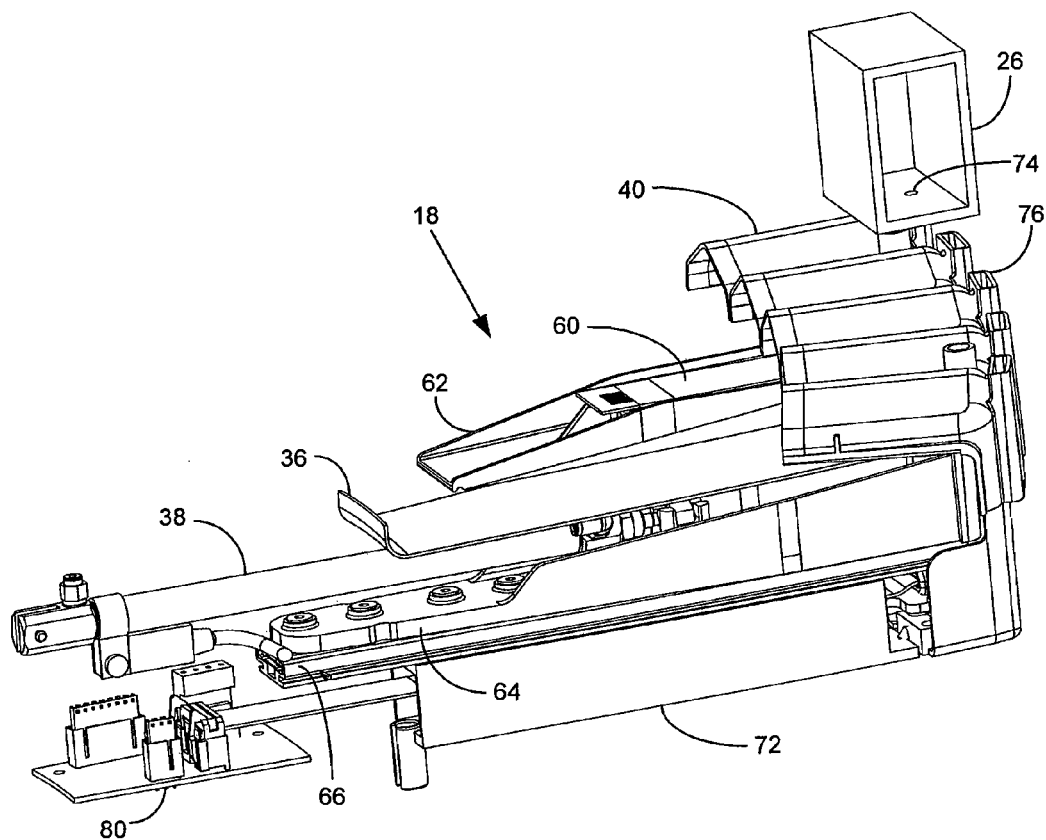
FIG. 6 is a perspective view diagram of an embodiment of a substrate holder mounted on a sample rail that includes an air cylinder that moves the substrate holder from a processing position and an access position. Also shown in FIG. 6 are splash shields and ambient air ducting utilized in some embodiments to assist in thermally isolating different substrate holders.

FIG. 6 shows in perspective a single cell 18 in a processing position within the exterior of the apparatus. In addition to the features shown in FIG. 5, FIG. 6 also illustrates in cut-away view, a section of gas conduit 26 having a hole 74 (that is one of many holes that make up a manifold of such holes leading from gas conduit 26) situated above a secondary gas conduit 76 that directs a gas, such as ambient air, across a substrate 60 held on heater platform 62. Pan 36 also is shown in cut-away view under the heater platform 62. A printed circuit board 80 through which electrical commands and power are provided to the cell also is shown. Gas cylinder 38 that is used to move the cell from a processing position (as shown) to an access position (as shown in FIG. 6) also is illustrated.

Figure 7:
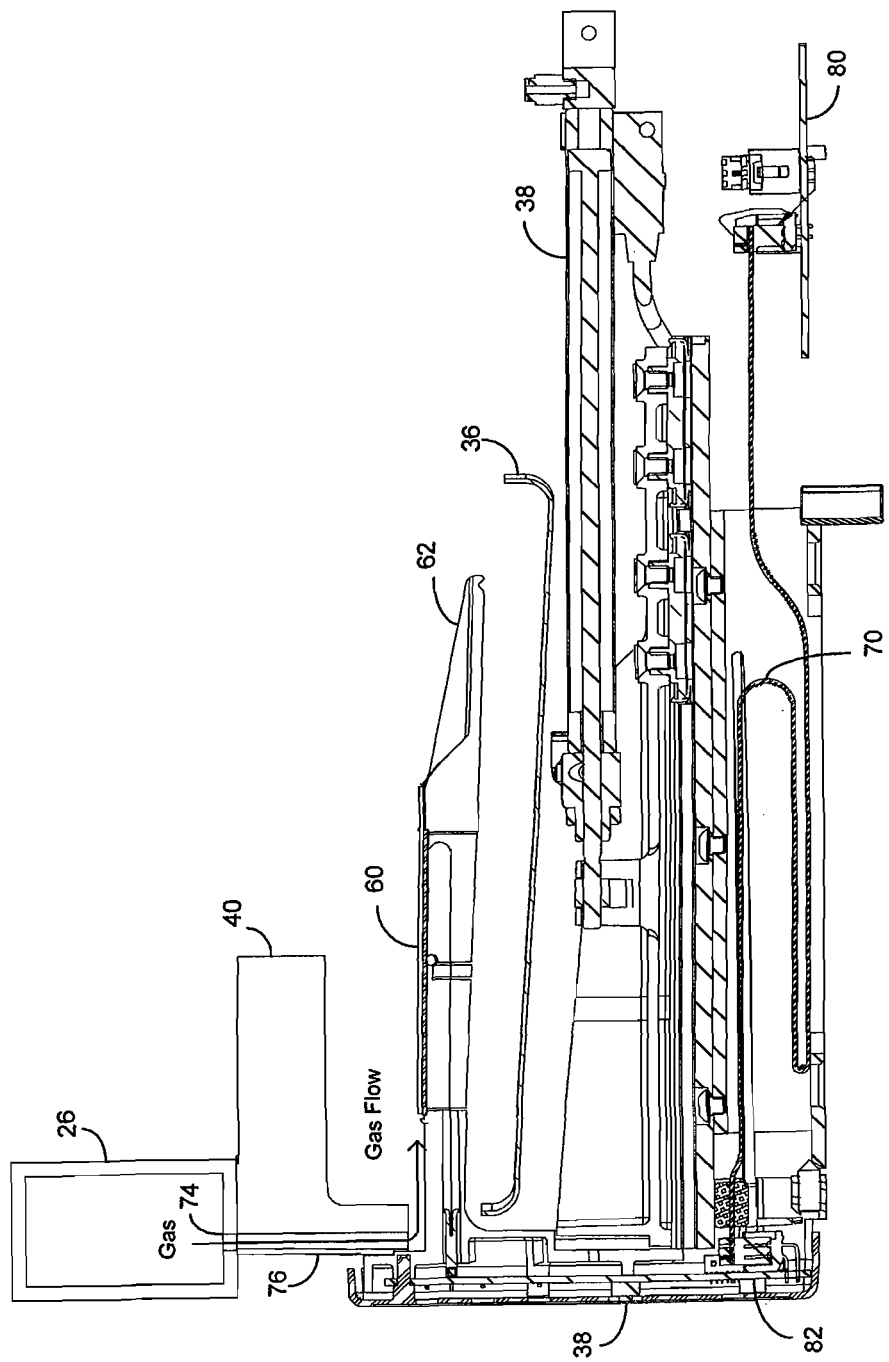
FIG. 7 is a side view diagram of an embodiment of a substrate holder illustrating how gas flow from a gas manifold is flowed past a substrate holder in a processing position to improve thermal isolation between different substrate holders of the disclosed apparatus.
Figure 8:
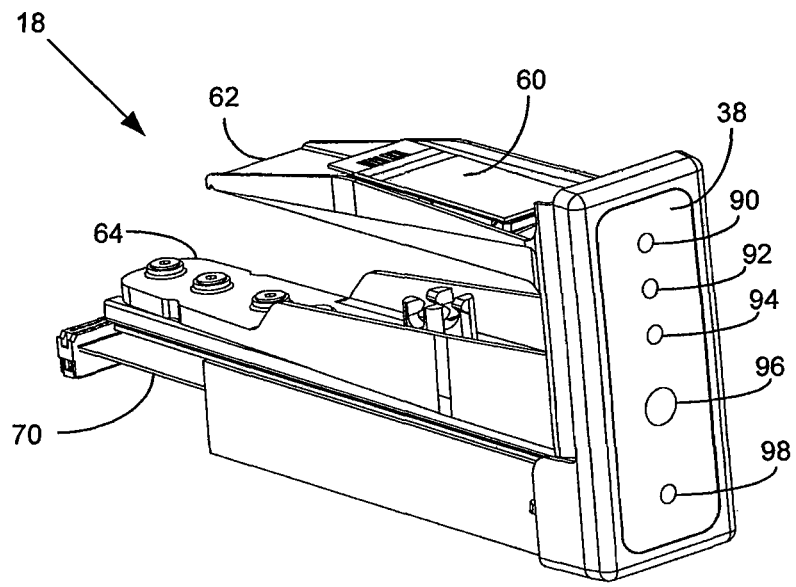
FIG. 8 is a perspective view diagram of an embodiment of a substrate holder including a sensor on its exterior surface, and in this particular embodiment, a plurality of status indicators also are shown beneath a covering layer.

FIG. 7 shows a single cell in cross section. Additional features of the cell illustrated in this figure are a second printed circuit board 82, located just behind exterior portion 38 that is connected to printed circuit board 80 through flex cable 70. FIG. 8 shows a single cell in perspective as it is be viewed from the exterior of the apparatus. Located under exterior portion 38 (which can be a flexible covering) are LED lights 90, 92, 94, and 98. Also under exterior portion 38 is a touch sensor 96. In one embodiment, top LED 90 is green and when on steady, indicates that the cell is empty. When flashing, it indicates that the cell contains a finished sample. Second LED 92, is amber and when on steady, indicates that the cell is processing a sample. The third LED 94 is red, and when flashing, indicates an error condition. The bottom LED 98 is blue, and is used for indicating a cell that contains a sample asked for by a particular sort (such as by patient). Sensor 96 can be a momentary contact switch that is used to open or close a cell. In a particular embodiment, exterior portion 38 is a Mylar cover sheet that covers the outer surface and has holes (or transparent portions) matching the position of the LED's that allow light from the LED's to shine through the Mylar cover.

Figure 9:
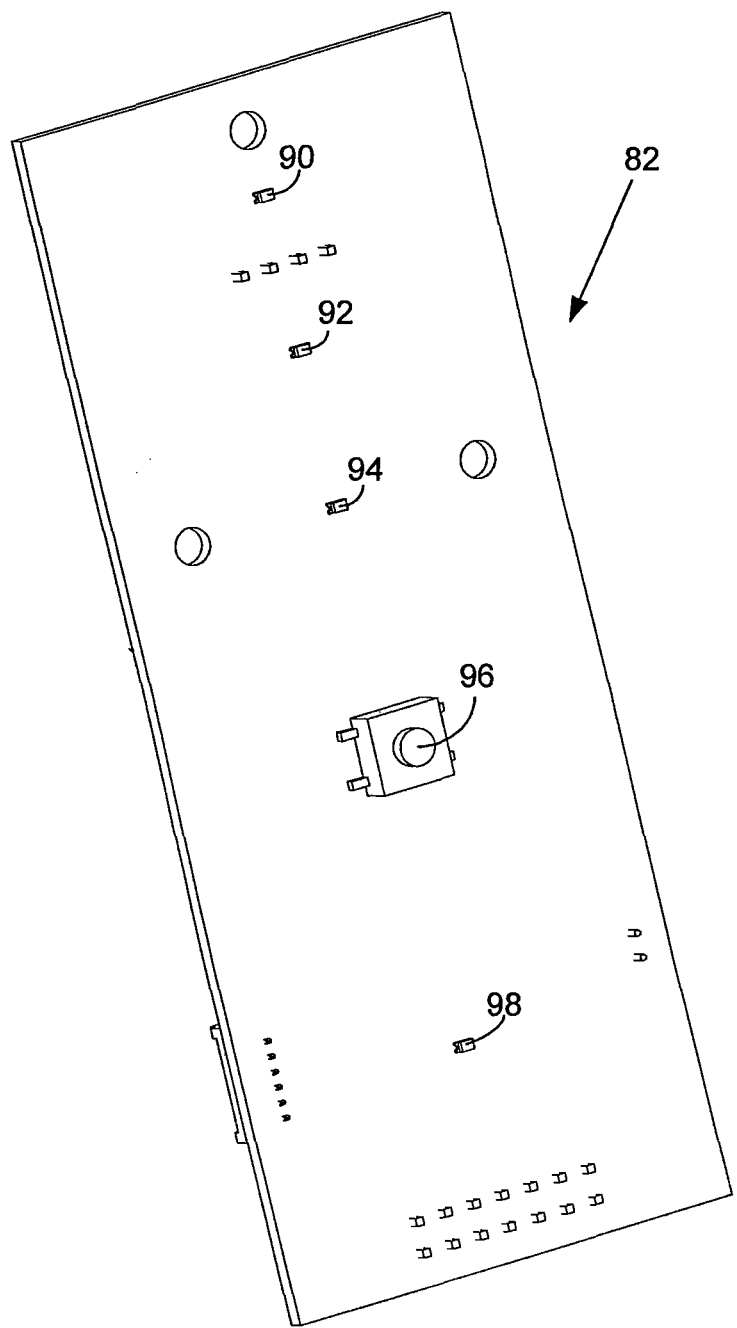
FIG. 9 is a perspective view diagram of a printed circuit board (PCB) underlying the covering layer illustrated in FIG. 8, including a touch sensor and a plurality of status LED lights of a plurality of colors, each color or combination of colors alerting a user to a particular condition.

FIG. 9 shows second printed circuit board 82 with its covering removed, to which circuit board are connected LEDs 90, 92, 94, and 98 and sensor 96, in this case a touch sensor for activating a touch command to move the cell between a processing position and an access position.

Figure 10:
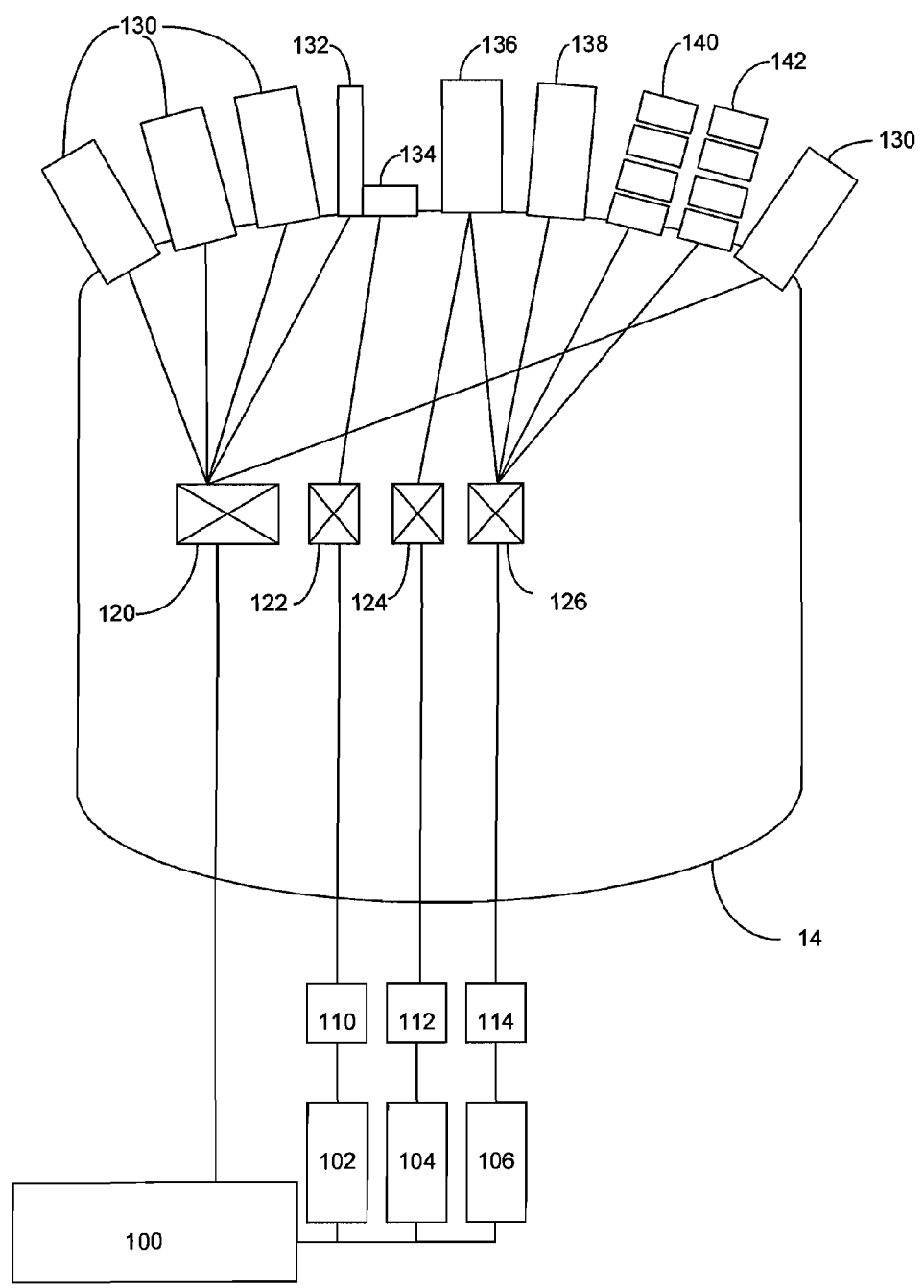
FIG. 10 is a schematic diagram illustrating an embodiment of a plurality of nozzles arranged along a plate arc at a second end of an elongate nozzle plate that illustrates typical types of fluidic connections made to supply different types of nozzles for performing a plurality of substrate processing operations.

FIG. 10 illustrates an embodiment of how nozzles on a nozzle plate 14 can be connected to bulk substrate processing fluid sources and to a source of compressed air. In this embodiment, compressed air source 100 is used to move fluids from large bulk reagent containers 102, 104 and 106 to smaller reservoirs 110, 112 and 114. In an alternative embodiment, a peristaltic pump is utilized to move fluids from the large containers to the smaller reservoirs. Although not shown, level sensors can be included in each of the reservoirs, and since there are separate large and smaller reservoirs, reagents can be added to the apparatus "on-the-fly" to the large reservoirs when they are empty while substrates are processed using the remaining reagent in the smaller reservoirs. A plurality of valves 120, 122, 124 and 126, which can themselves include a plurality of separate valve arrangements in different settings, are used to direct compressed air and reagents toward appropriate nozzles 130, 132, 134, 136, 138, 140 and 142 at appropriate times, for example, under computer/microprocessor control.

Figure 11:
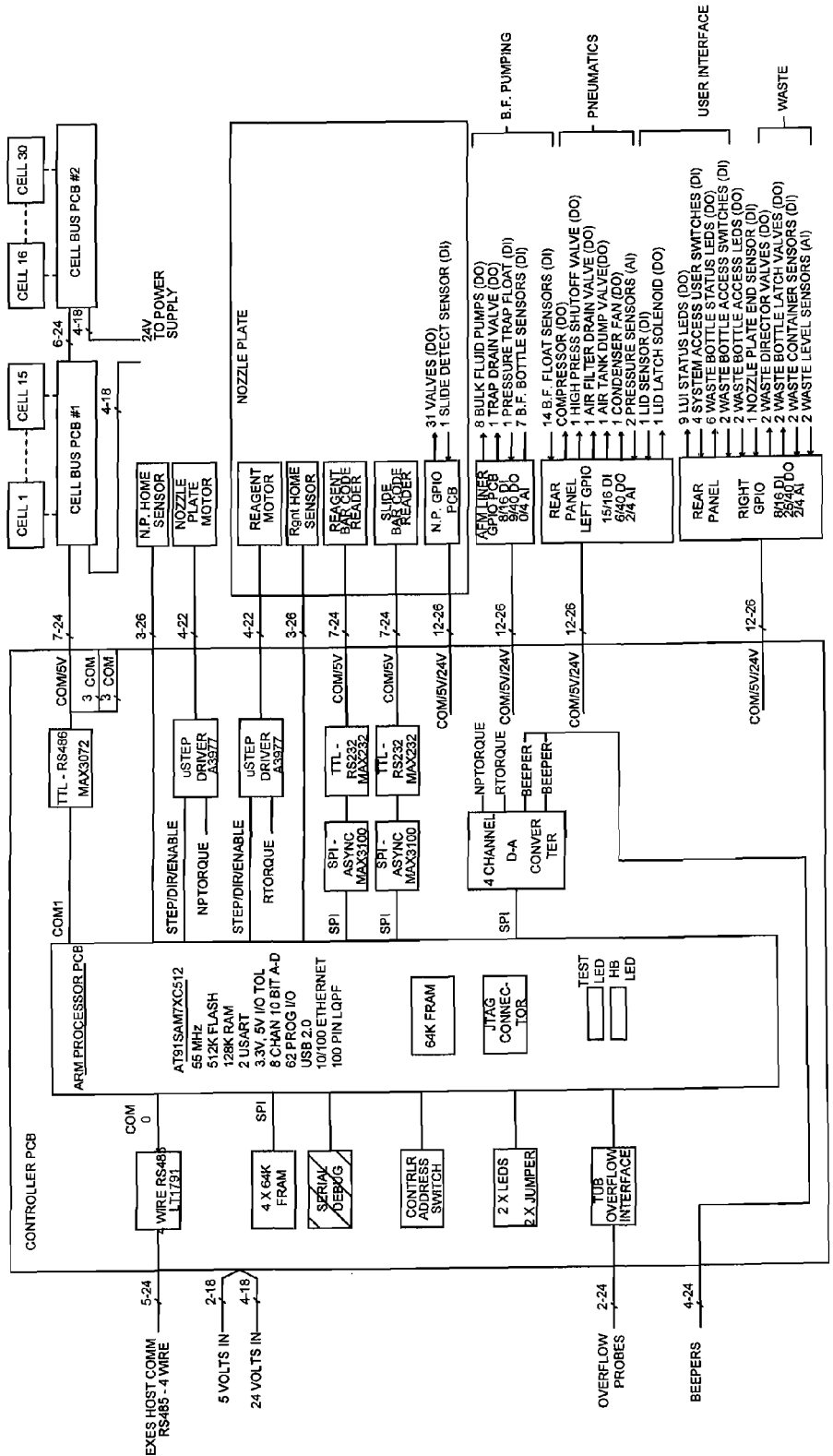
FIG. 11 is a schematic diagram illustrating an embodiment of electrical and data transmission for independently processing a plurality of substrate-supported samples.

FIG. 11 shows a schematic of the electrical connections/data connections of an embodiment of the disclosed apparatus. In addition to the connections illustrated, the disclosed apparatus can be connected through its controller PCB to additional devices (such as additional substrate treatment apparatuses, imaging stations, accessioning stations, cutting stations, other computers, databases, servers and the like) as are discussed in co-pending U.S. patent application Ser. Nos. 11/032,324 and 11/818,223 entitled "Laboratory Instrumentation Information Management and Control Network," which applications are incorporated by reference herein.

Figure 12:
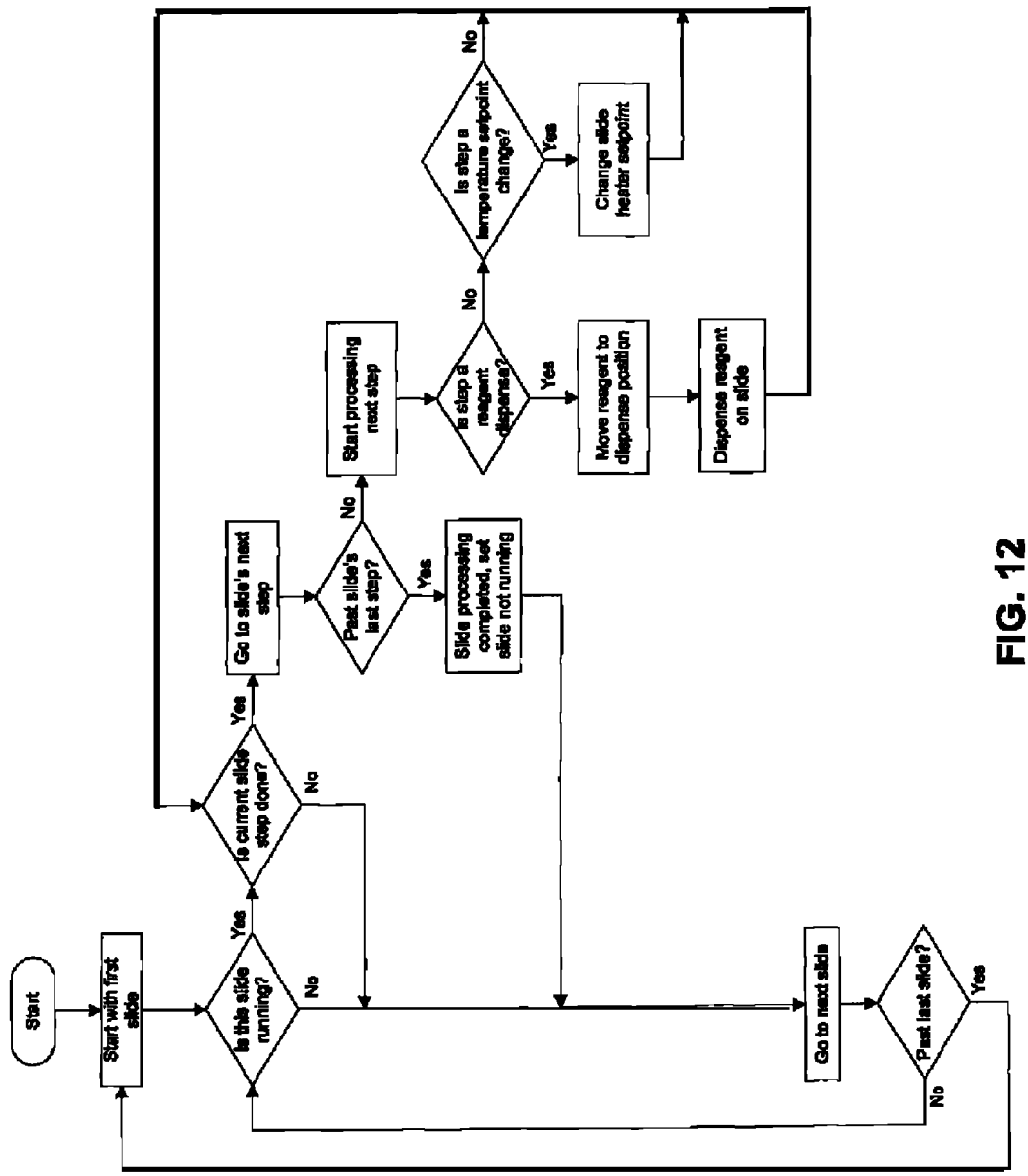
FIG. 12 is a flowchart illustrating an embodiment of a computer logic scheme for substantially continuous and simultaneous processing of a plurality of samples according to different processing protocols.

FIG. 12 shows a flowchart illustrating an embodiment of a method for simultaneous processing of a plurality samples in the disclosed apparatus. As the nozzle plate is moved past the substrate processing cells, substrate (such as slides) are detected, their processing status is assessed, and appropriate nozzles/devices are moved into place as needed. Once the nozzle plate has gone past all the samples that are being processed at a particular time, the nozzle plate is rotated back toward a first sample in the arc and the process of moving the nozzle plate past the cells resumes.

In one embodiment, all substrate treatment protocols have multiple "pause points" defined where no reaction/treatments are active. At these places in a protocol, a substrate can be covered with a neutral, non-reacting buffer while the staining sequence is paused. If all the samples are paused simultaneously, the staining operation can be stopped and new dispensers or vials added or removed, for example, to or from the reagent carousel. These pause points are called "landing zones." However, using a landing zone to add or remove reagents causes the total time for substrate treatment to increase, so their use is typically minimized.

In addition to the devices illustrated in the figures discussed above, it is also possible to add a camera for imaging substrates before, during and/or after processing. Imaging can be utilized for quality control or for actual transmission of an image to a health professional or researcher for interpretation.

Example 2

Railed Sample Aspirator Unit

In one embodiment, a railed sample aspirator unit is utilized to remove residual reagents from a substrate. The railed aspirator unit can include discrete rails (see, for example, U.S. Patent Application Publication 2006/0019303, which is incorporated by reference herein) and can further include reagent dispensing means. However, in the particular embodiment discussed in this Example, an improvement to such a system is disclosed that allows the aspirator head to use the substrate as a reference surface for accurately controlling the gap between the head and the top surface of the substrate without disturbing a sample on the top surface of the substrate. A second improvement is to have two sets of vacuum holes, one pulling liquid from the small gap that is formed between the bottom of the vacuum head and the top of the substrate and the other set pulling liquid from the top of the puddle that builds in front of the advancing head as is moves out over the substrate. The second, upper set of holes draws the lower density liquids that might be floating on the aqueous puddle, preventing them from getting contacting and possibly damaging the sample.

Figure 13:
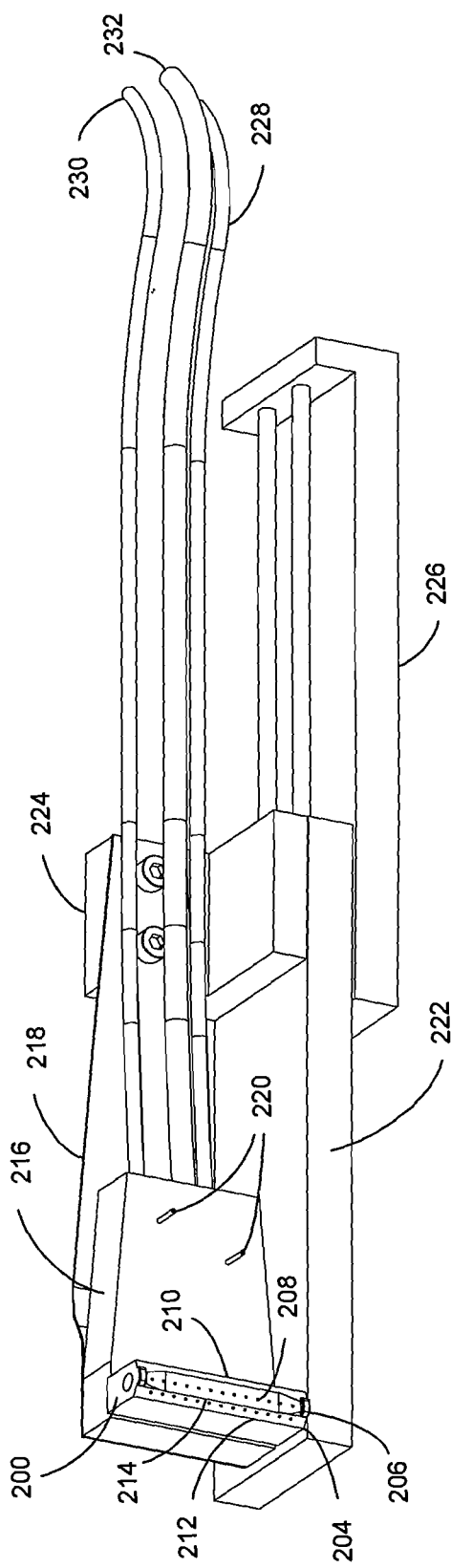
FIG. 13 is a perspective view diagram of an embodiment of a railed sample aspirator where the "rail" comprises the aspirator riding along an edge of the substrate.

FIG. 13 shows a perspective view of an aspirator head 200 and associated means for moving the head across a substrate and for supplying vacuum and reagents to the head. Aspirator head 200 includes outer suction holes 204, guide surface 206, lower suction holes 208, bottom surface 210, upper suction surface 212 and upper suction holes 214. Aspirator head 200 is attached to dispense nozzle manifold 216 that is attached to dispense nozzle spring 218 that functions to push aspirator head 200 against a substrate. Included on dispense nozzle manifold 216 are dispense nozzles 220. Dispense nozzle spring 218 is connected to actuator assembly 222 through bracket 224. Extended actuator portion 226 includes rails along which actuator assembly 222 is movable. Line 228 provides a first rinse fluid to the dispense nozzle manifold 216, and line 230 provides a second rinse fluid to the dispense nozzle manifold 216. Vacuum line 232 provides a vacuum connection to the various suction holes. Lines 228, 230 and 232 can pass through an energy chain, not shown, then onto valves, also not shown. The valves can be automatically sequenced under computer control to open and close at appropriate times. A line can be plumbed permanently to a rinse fluid through a two way valve, or to a distribution valve that can connect any of several fluids. Rinse fluids can then easily be changed by simply actuating the valve for the next fluid.

Figure 14:
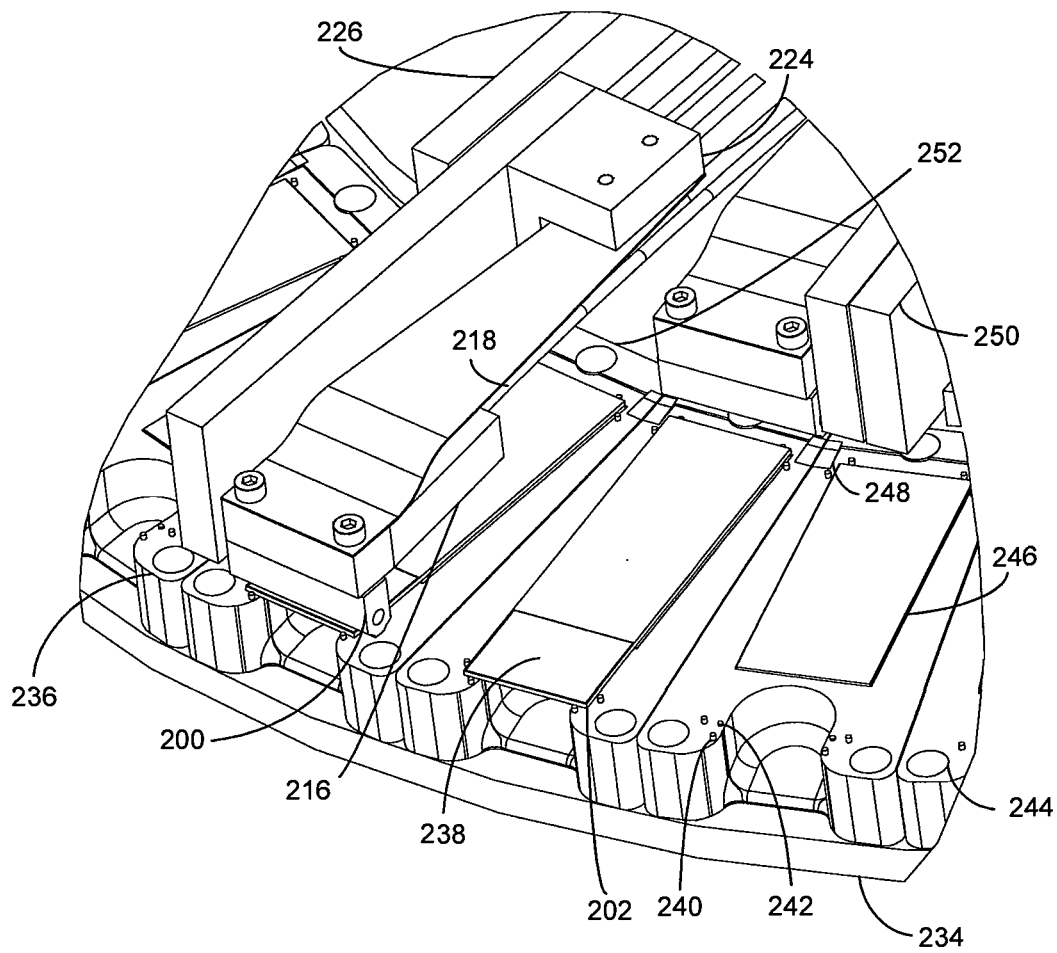
FIG. 14 is a perspective view diagram showing an embodiment of a moveable substrate aspirator mounted on a nozzle plate, where the substrate aspirator is positioned above a particular substrate held in a particular substrate holder.

FIG. 14 shows an aspirator head 200 positioned over a substrate 202 in a disclosed substrate processing apparatus (cell separation removed for clarity). In addition to the features discussed with regard to FIG. 13, FIG. 14 shows a support 234, a molded heater base 236, a label 238 (such as a barcode label) on substrate 202, substrate locator pins 240 on molded heater base 236, substrate tip support 242, rubber plug 244, a stainless steel heater plate 246, and ramp 248, which ramp functions to ease the aspirator head onto the surface of a substrate from raised land 252. A retracted aspirator head is shown as 250.

Figure 15:
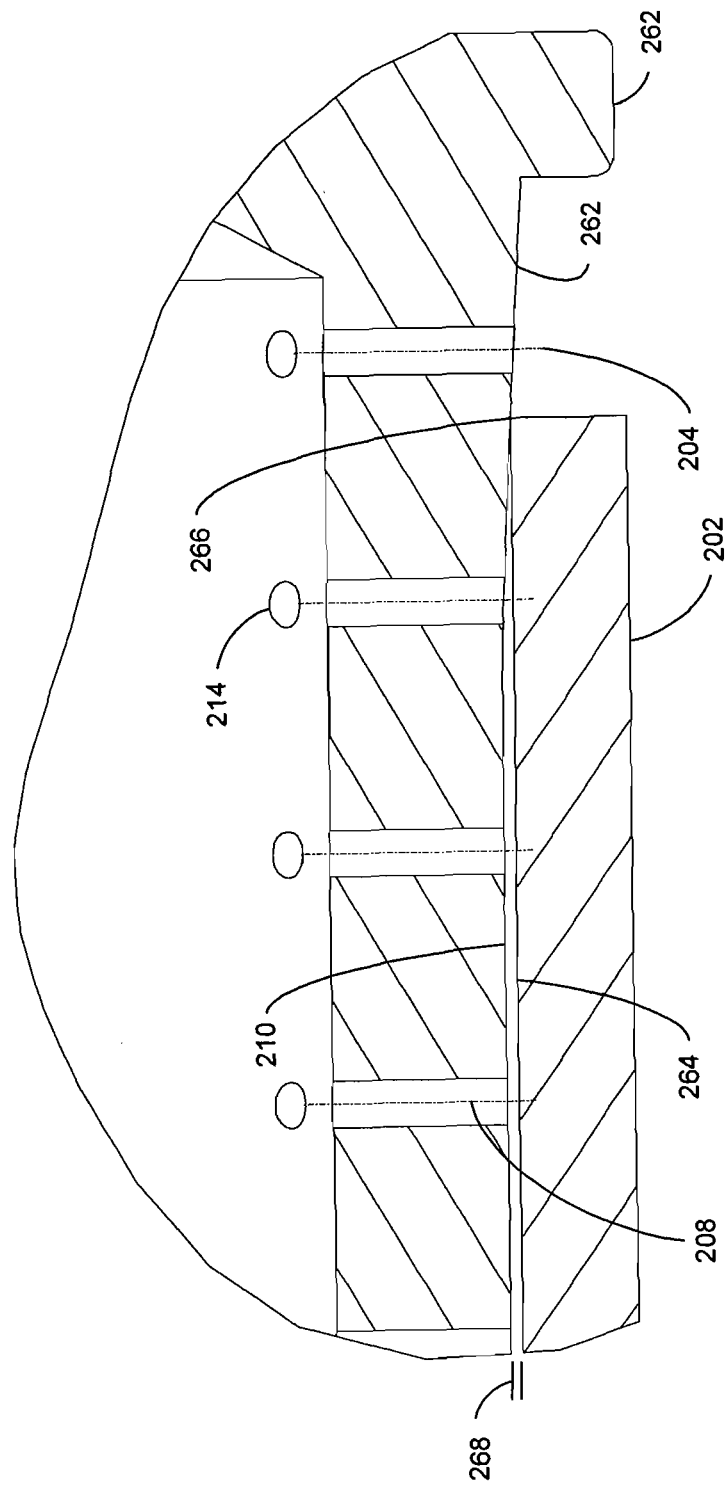
FIG. 15 is cut-away view diagram of an arrangement of nozzles in an embodiment of a substrate aspirator showing an arc configuration of a lower surface of the substrate aspirator contacting an edge of a substrate such that the substrate edge functions as a rail on which the aspirator rides.

FIG. 15 is a cross-section diagram showing a bottom surface 210 of an aspirator head in contact with substrate 202 at a top corner 266 of the substrate, but otherwise held above top surface of the substrate 264. Also illustrated (in addition to other features already discussed above) are a sloped-surface 260 of the bottom of the aspirator head, and a guide surface 262 that can be used to raise the aspirator head off of a substrate. As can be seen in FIG. 15, there is a gap 268 between the bottom of the aspirator 210 and the top of the substrate 264, which varies as a consequence of the sloped surface 260.

The technique for removing reagents from the substrate enabled by the disclosed aspirator includes vacuuming off the residual fluids by means of a vacuum head that has a lower surface that is parallel to the top of a substrate and displaced upward from it by a small gap of about 130 microns. There are series of small holes in this bottom surface that connect to a source of vacuum to draw off liquid from the top of the substrate. The improvement is that the bottom surface is maintained at a fixed but small distance above the substrate by means of a slightly sloped surface of the vacuum head that is above the edges of the substrate. This slightly-sloped surface contacts the outer, top corners of the substrate, which top corners function as a "rail." That is, the vacuum head contacts the substrate and translates along it but does not contact a substantial portion of the top surface of the substrate where the sample is placed. It only contacts the top corners of the substrate. At a three degree angle, it rises to five microns of height (typical tissue thickness) when only 57 microns in from the edge, so at most, 57 microns of a sample could be affected by translating this vacuum head along the length of the substrate. This is less than 0.5% of the total width of the substrate. Because of the small angle (3°) of the slope on the vacuum head where it touches the substrate, variation in the width of the substrates produce a small variation in the height between the substrate and the head. For the entire range of microscope slide substrates used throughout the world, the height variation is ±30 microns from a nominal of 130 microns. This covers microscope slides as narrow as 24.8 mm (US) and as wide as 26.1 mm (Japan). This gap variation of 100 to 160 microns is tolerable for the proper functioning of the vacuum head.

When retracted, the vacuum head is radially inward from the active end of the substrate. To vacuum off reagent, the vacuum head is extended radially outward, over the substrate, all the way to the end, vacuuming reagent as it goes, leaving very little residual liquid. There are a pair of dispense nozzles, one on each side of the centerline of the substrate, that are positioned radially inward from the vacuum head. Rinse fluid can dispensed onto the substrate through this pair of nozzles that follow the vacuum head as the head is moving radially outward, thereby wetting the recently vacuumed substrate a few milliseconds after the head has passed. The vacuum head is then retracted, radially inward, mixing the just applied rinse fluid with the small amount of residual that remained after the first vacuuming pass. The residual liquid left on the substrate after suction is on the order of ten µl. The rinse volume added can be, for example, 300 µl. With four vacuuming cycles, the dilution is $(10/310)^4=10^{-6}$.

Example 3

Radiant Thermal Control Unit

Certain substrate processing steps utilized in immunohistochemical (IHC) and in situ hybridization (ISH) analyses (for example, cell conditioning, antigen retrieval, target retrieval, nucleic acid denaturation, nucleic acid hybridization and the like) have increased the desirability of achieving higher and more accurate sample temperatures. Conductive heating suffers from several drawbacks when attempting to elevate the temperature of a substrate and a sample thereon, particularly when attempting to elevate the temperature above about 80° C. and more particularly above about 100° C. Ideally, the temperature of the heater and the temperature of a substrate touching the heater are identical, but any gap between the heater surface and the substrate presents resistance to heat flow and causes different parts of the substrate to have different temperatures. The thermal resistance across a substrate depends on heater and substrate flatness and whether any gaps between the heater and the substrate are filled with liquid or air. Additionally, the flatness requirement places a limit on how thin a heater plate can be constructed. The higher the degree of flatness needed, the thicker the plate must be, and the thicker the plate, the greater its thermal mass, which limits the rate at which the temperature can be changed.

If instead an air gap is used between a heater and a substrate such that the heater and the substrate do not touch at all, heater plate flatness is no longer as great a factor in determining homogeneity of the temperature profile across a substrate. In this instance, heat transfer is primarily radiative and not conductive. In such a configuration, there will be a significant temperature difference between the heater and the substrate, but the heat transfer is more even across the substrate. Predicting the temperature of the substrate for a given heater temperature is possible, but a more effective solution is to utilize an infrared sensor that directly measures substrate temperature without requiring contact of the sensor with the heater or the substrate. Furthermore, an infrared sensor permits not only direct measurement of substrate temperature, but also sample temperature and the temperature of a liquid held on a substrate (such as covering a sample). Non-contact infrared temperature sensors are available, for example, from Exergen, Inc. (Watertown, Mass.), Perkin Elmer (Waltham, Mass.), Raytek (Santa Cruz, Calif.) and Mikron (Oakland, N.J.).

The relative placement of the radiant heater, the substrate and the IR sensor can affect the substrate temperature uniformity that is achievable. In some embodiments, the radiant heater is positioned below the substrate, leaving a substantially uniform air gap between the heater and the substrate of from about 0.5 mm to about 3.0 mm, for example, a substantially uniform air gap of about 1.0 mm. Placement of the heater below the substrate and the sensor above the substrate eliminates the potential for the heater and the sensor to interfere with one another. While it is possible to place both the heater and the sensor on the same side of the substrate, this configuration requires a hole in the heater through which the sensor can detect the substrate temperature. The hole in the heater will make it more difficult to maintain substrate temperature uniformity and does not make it easy to measure the temperature of an upper surface of the substrate, the temperature of a sample on the upper surface of the substrate or the temperature of a liquid on the upper surface of a substrate. If the sensor is placed between the substrate and the heater, the sensor will block the radiant heat flow, again causing substrate temperature uniformity.

As suggested above, another benefit of not having the heater touch the substrate is that the flatness of the heater is not as important to substrate temperature uniformity. As a consequence, the heater can be made very thin, thereby reducing the heater's thermal inertia and permitting increased rates of substrate temperature change, both higher and lower.

Figure 16:
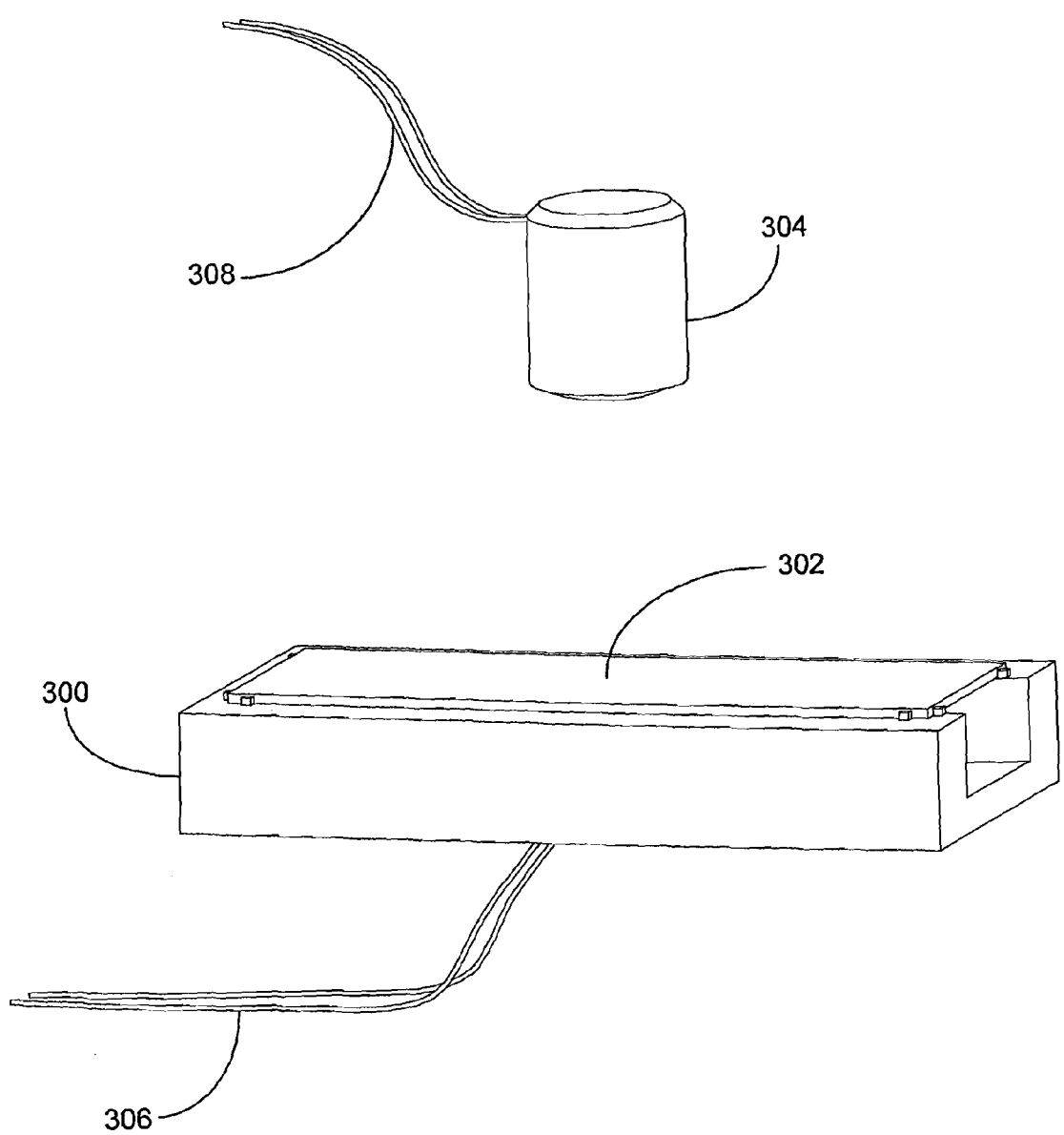
FIG. 16 is a perspective view diagram of an embodiment of a radiative thermal control unit of a substrate holder with a substrate in place and a non-contact sensor aimed at the substrate surface to measure a surface temperature.

One embodiment of a radiant heater and infrared sensor configuration is shown in FIG. 16. In this figure, a substrate 302 is placed on thermal control unit 300. Infrared sensor 304 is positioned above substrate 302 such that its field of view coincides with one or more of the top surface of the substrate, a sample on the top surface of the substrate, and a liquid on the top surface of the substrate. Electrical leads 306 to thermal control unit 300 and sensor leads 308 can be part of closed loop electronics (not shown) that work to maintain a preselected setpoint temperature of one or more of the top surface of the substrate, a sample on the top surface of the substrate, and a liquid on the top surface of the substrate.

Figure 17:
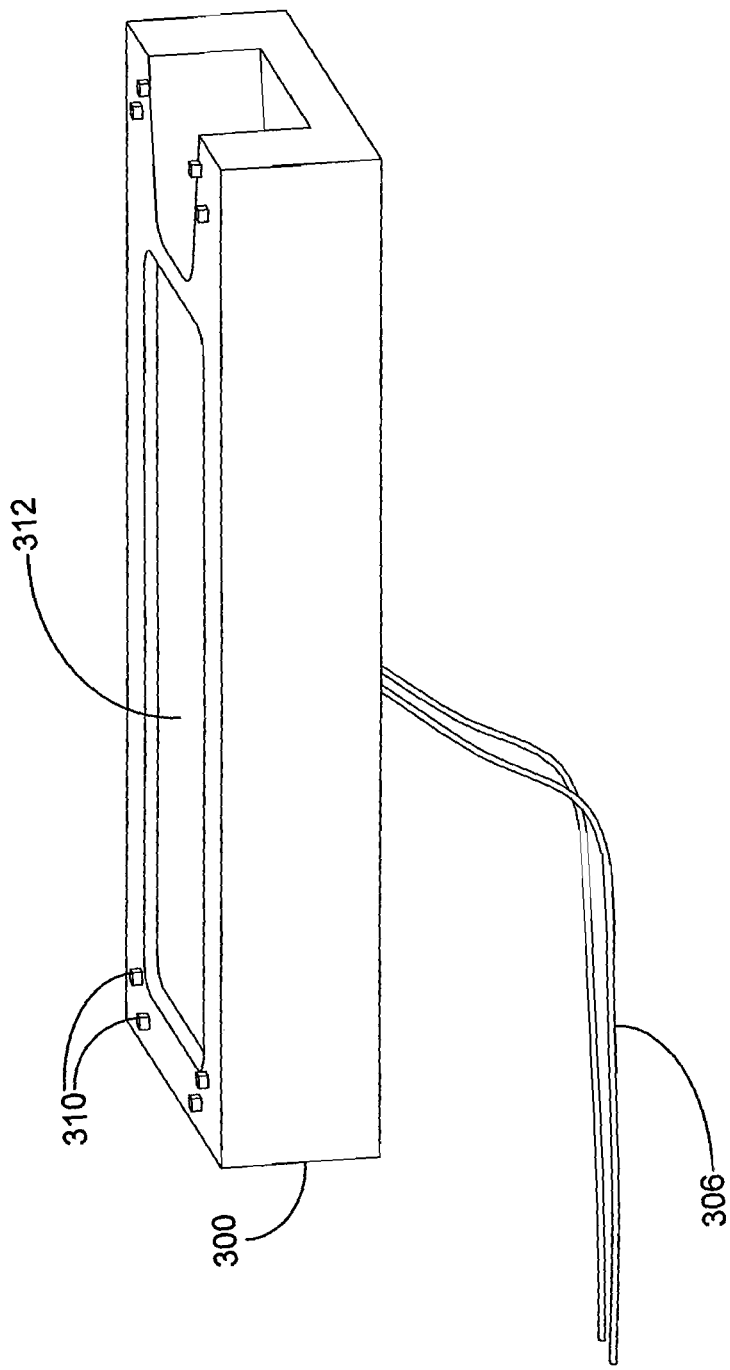
FIG. 17 is a perspective diagram of the lower portion of a radiative thermal control unit of a substrate holder illustrating the cavity that forms an air gap between the heated lower surface and a substrate placed onto the thermal control unit.

FIG. 17 illustrates the thermal control unit 300 with the substrate removed to reveal, in this embodiment, a radiant heater 312 located below the top of the unit. Also shown in FIG. 17 are fiducials 310 that hold a substrate in place.

Example 4

Instrument Control

An apparatus, system, and a machine-readable medium having stored thereon the instructions for controlling processing of samples in different sample cells was created to accommodate the entire set of state transitions from Startup to Running and back again to a state where the instrument can be loaded with new samples, which is a mode referred to as "Run Access." Also described is implementation of Landing Zones, which permit a user to add/change reagents on the instrument with minimal disruption of the processing of samples being currently processed.

In one embodiment (as outlined in the flow diagram of FIG. 18), the run startup state machine requires a user to depress the "on" button (also referred to as the "Bug" button herein) on the Sample Access Panel to place the staining instrument into Access Mode. Access Mode allows the compressor to be started, thus providing pressure that allows access to the sample chambers. During this mode, the reagent hood can be accessed for loading and unloading of reagents. Samples can be added to the sample chambers without triggering a nozzle plate move for sample detection and barcode read. In order to progress to the next state, the user will need to select the Run Button from the host application.

When the Run Button is selected, the state machine moves into Run Startup Mode. This mode will:
    lock the reagent hood,
    prime and purge the bulk fluids,
    home the reagent carrousel,
    and home the nozzle plate.
Once these activities are completed, the state machine moves into Run Batch Standby Mode.
Barcode Reading During the Run Batch Standby Mode, the reagents on the reagent carousel are read and a request is made from the host application to retrieve the barcode data for the read.
    Read the reagent barcodes starting from position 1 through position 35
    The remote software stores the data from each reagent barcode read
    The host software requests the reagent barcode data to be returned to the host application through a host command and receives an appropriate response.
    The host application qualifies the reagents loaded on the reagent carousel based on
        Product is registered in the database
        Correct instrument type
        Sufficient tests remaining
        Valid expiration date
        Active reagent status
            Positioning on the carousel (certain reagents are required to be side-by-side)
Failure to qualify any of the reagents will return the state machine to Access Mode. The reagent hood will be unlocked to allow access to the offending reagents.

Next, the nozzle plate starts moving from sample to sample to perform sample detection in each of the sample chambers that were opened while in Access Mode. When a sample is detected, the sample barcode reader will read the barcode data. The host application will request a retrieval of the sample barcode data.
    Move to the first position in which a sample drawer was opened, detect and read the sample barcode if a sample is in the position
    Move to the next sample position, detect and read the sample barcode, repeat until all samples are read
    The remote software stores the data from each sample barcode read
    The host software requests the sample barcode data to be returned to the host application through a host command
    The remote software sends the barcode information to the host application in a response message
    The host application qualifies the protocol assigned to the case sample based on
        Protocol is in the database
        Correct instrument type
        Protocol steps matching staining procedure steps
        The necessary reagents needed to perform the staining procedure are loaded on the reagent carousel
Failure to qualify any of the protocols will return the state machine to Access Mode. The reagent hood will be unlocked to allow access to the reagents and sample drawers.

Once the barcode reading is complete and protocols and reagents have been qualified, the state machine will move to the Run Standby Mode. The host application will compile and download the macro steps for each sample position to the remote. Once the download is complete, the state machine will move to Running Mode.
Running Samples are processed in lock step during the Running Mode. Any samples added during this mode will be detected in lock step with the samples currently being processed. The sample will be detected and read as the nozzle plate continues stepping past the new sample. The host application will
    request the barcode data,
    qualify the protocol,
    qualify the reagents are available,
    compile the macro steps
    download the macros to the remote software
    start the staining process for the samples that were added
This activity happens without impacting the staining process on currently running samples.
Completed Samples State When all the samples have completed their respective staining processes, the state machine moves to Run Standby Mode. While in this mode, the reagent hood is locked and not accessible for adding/removing reagents. The internal reagent hood flag will be initiated to FALSE and cannot be changed.

Figure 18:
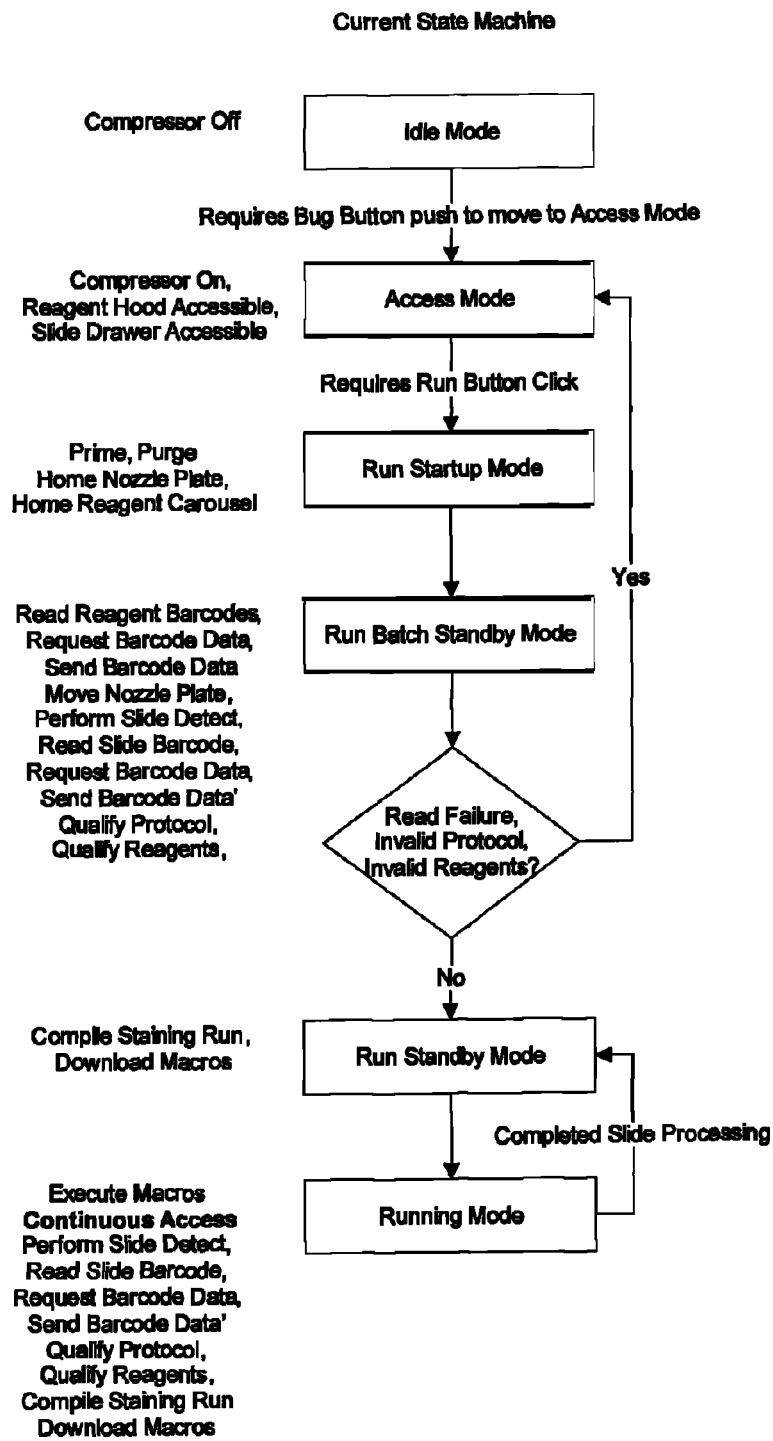
FIG. 18 is a flow diagram of an embodiment for initiating the instrument Access Mode.

Once the sample drawer is open and closed, the nozzle plate is homed and begin the sample detection, barcode read, compile and download process and ultimately begins moving through the state machine again. In the embodiment of FIG. 18, there is currently no capability for the user to return the state machine to Access Mode to allow access to the reagents.

Figure 19:
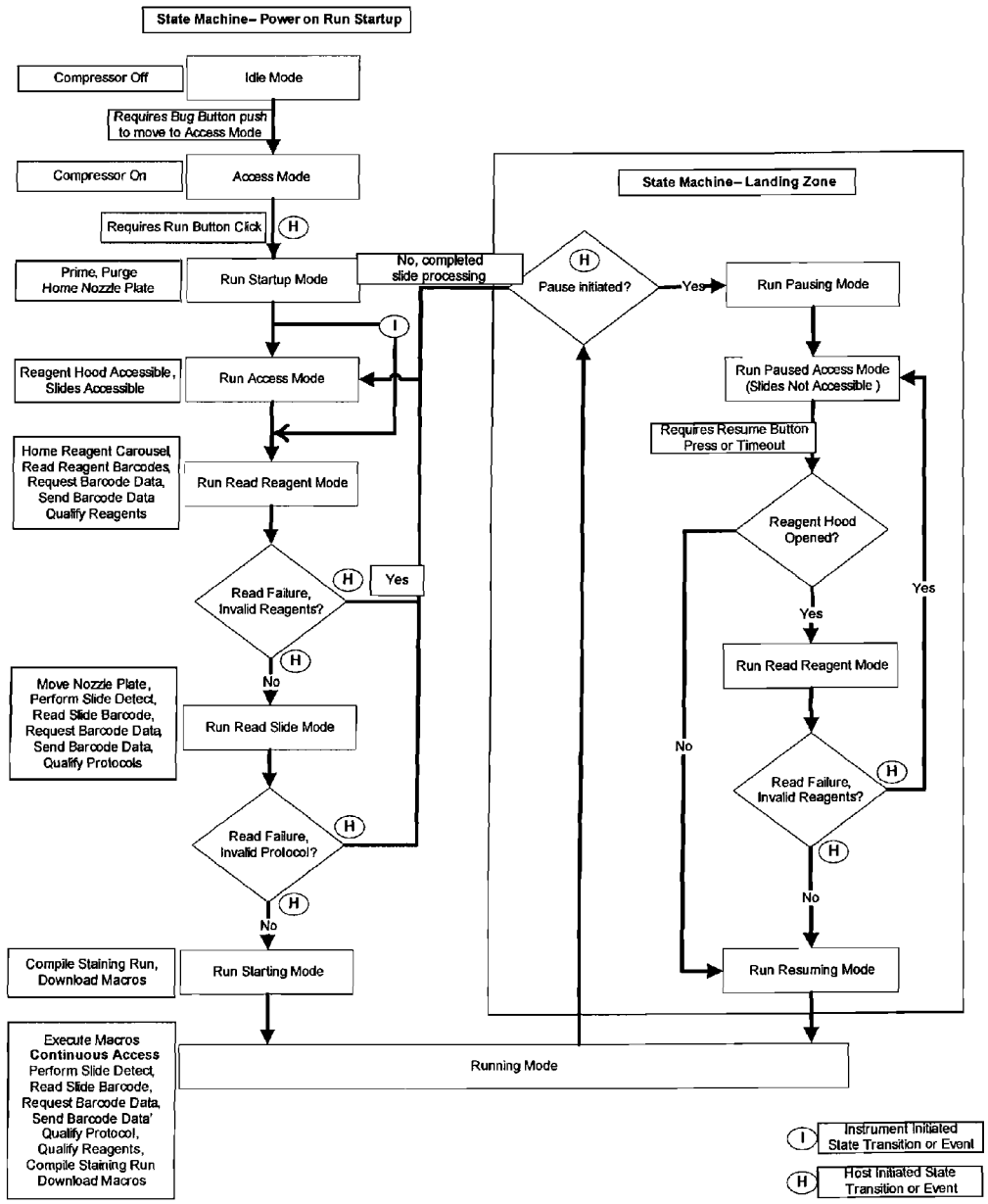
FIG. 19 is a flow diagram of an embodiment comprising Landing Zones enabling access to reagents while the instrument is continuing to process samples therein.

A second embodiment that includes Landing Zones to permit access to reagents while samples are in process is shown in the flow diagram of FIG. 19. Under normal running conditions, samples execute against individual 'macro zero' steps to perform their staining procedures. Under these optimal conditions, samples are processed without regard to outside issues such as other samples running, user interventions, instrument pauses, etc. While these may be optimal conditions for individual samples, this is less than optimal for lab technicians running the instrument, because throughput can be adversely affected when reagents run low or need to be changed.

To increase usability of the instrument in the lab environment, the apparatus and system can incorporate 'pause points' in most sample procedures, which are potential points in sample processing procedures where a sample can safely be paused, for a short amount of time, without adverse effects to the sample staining. The instrument can be told to pause samples being processed, by informing the instrument at which macro zero step to stop each sample. This declares a 'landing zone' for the instrument as a whole, and affects the processing of samples currently running.

When the instrument is told to pause at a landing zone, the macro zero step to pause each running sample is passed to it from the host software, as generated from the defined pause points in the sample procedures. A check is performed for each running sample, comparing the step number it is currently processing against the requested pause step. All pause steps must be greater than the currently processing steps, or the instrument will refuse the request to pause all samples and will continue normal processing.

Upon acceptance of the command to pause at a landing zone, the instrument mode is changed to RunPausing, and each running sample successively has its state changed to RunPausing until all are paused. In other words, subsequent processing of samples continues, but only until each sample reaches a pause point macro zero step. Once processing for a particular sample has been performed on the pause point macro zero step requested, the sample state is changed to RunPaused. The nozzle plate position at the point the sample enters the RunPaused state is saved. When in the RunPaused state, no macro zero work is performed on that ssmple. Once every active sample has reached the RunPaused state, the instrument mode will be changed to RunPaused; and the instrument has achieved the landing zone.

Once the landing zone has been achieved the nozzle plate is moved to the center position, after which the nozzle plate and reagent tray motor torques are removed, making it as easy as possible for the operator to move them to access the reagents in the instrument. Once motor movements are complete, the cover lid lock is deactivated and the cover lid switch is monitored to detect if an operator opens the lid. An alarm will sound to inform the operator that the instrument is ready for the reagents to be accessed as required. Lastly, the instrument will start timing how long it has been in the landing zone, for later consideration.

Normal actions taken while at a landing zone include the operator opening the cover lid, changing some reagents, and closing the lid. In such a case, the reagents must be re-read and the host must confirm that reagents are available to process the samples in the instrument. The details of this scenario are described more fully below. Another possible scenario is one in which the operator does not open the cover lid in the amount of time defined in the landing zone. In this scenario, the landing zone is completed without operator intervention, the cover lid is locked and the nozzle plate and reagent tray are re-homed. After the landing zone has been completed via one of the scenarios above, and the cover lid has been locked and motors are once again in run position, the instrument mode is changed to Running, and each active sample will have its state changed to RunResuming. The nozzle plate will start regular marching, every 6 seconds. When the nozzle plate has reached the previously saved position for each sample, that sample's state will be changed to Running, and normal macro zero processing will resume. Thus, in summary and with reference to FIG. 20:

Landing zones are opportunities for the user to access the dispenser carousel to replenish available reagent inventory while the instrument is processing samples.
   Landing zones are defined by discrete pause point steps encoded in the staining procedures of the samples currently being processed on the instrument.
   Procedure writers insert pause point steps as frequently as necessary along non-critical areas of the staining process where the sample can sit unattended for a prolonged period of time.
   Landing zones are calculated dynamically by aligning on available pause points across all running samples' staining procedures (see, FIG. 20).
   Landing zones are opportunities for reagent carousel access, so if never exercised by the user, landing zones have no effect on the timing or the outcome of the samples being processed.
   If the user chooses to exercise a particular landing zone, the host instructs the instrument to pause each sample's staining process at the designated pause point.
   One sample at a time, the instrument will halt sample execution once the sample reaches the designated pause point.

Figure 20:
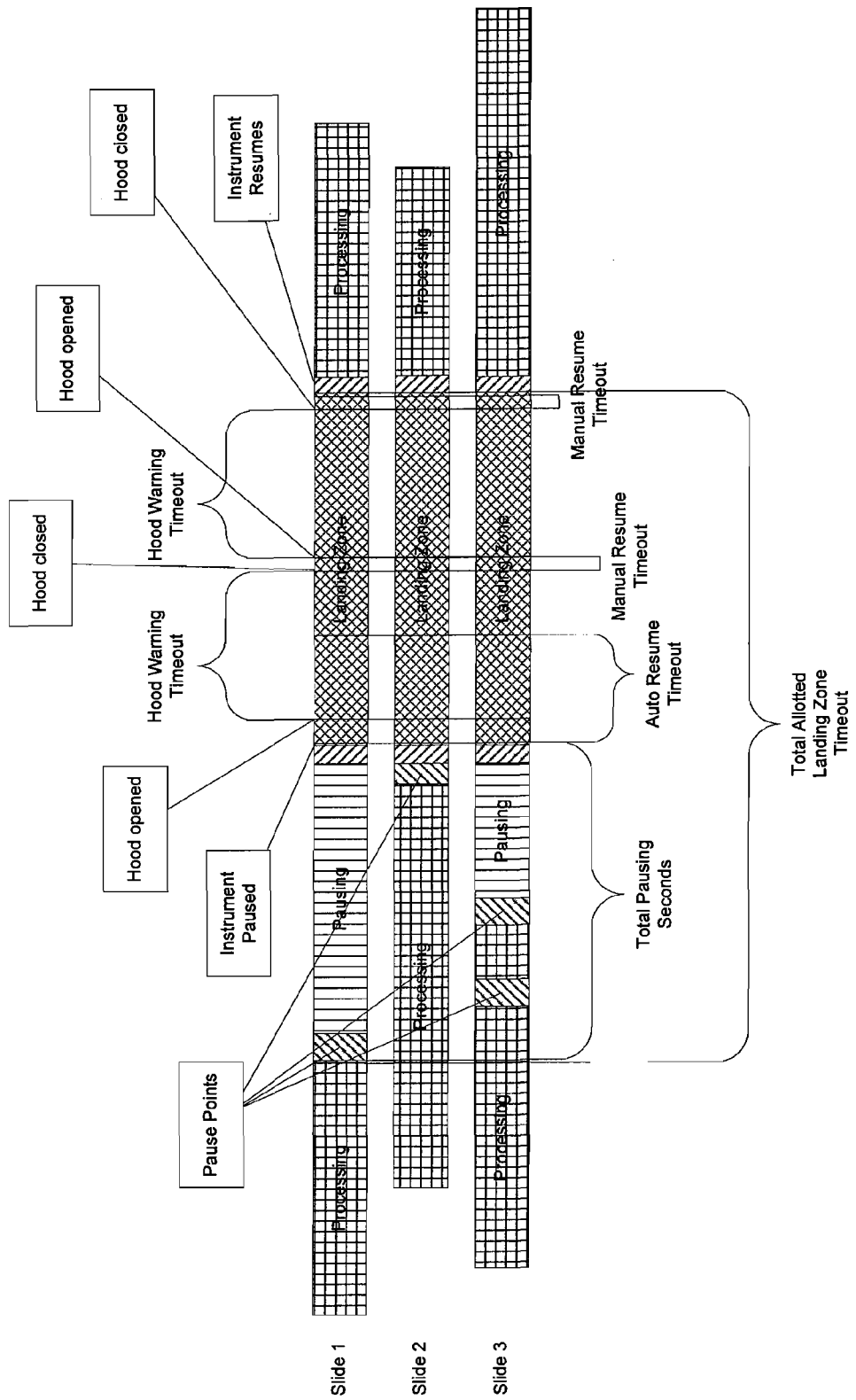
FIG. 20 shows flow diagrams of an instrument embodiment depicting the operational flow for three slides inclusive of Landing Zone operation and instrument operations thereafter.

Further details regarding the schemes of FIGS. 19 and 20 follow. In a second embodiment of a run startup state machine, the instrument is able to re-start the processing of new samples automatically, given an idle period that comes after completing other samples. A different state machine which accommodates this cyclical nature is described. This startup process can be initiated via many different sequences of states, for example:

1. From Idle mode (such as after a power cycle), the user presses the Run button in the user interface (UI), which primes/purges the instrument (Run Startup mode) and sends a message to enter Run Access mode.

2. From Access mode, the user loads samples, presses the Run button in the UI, which purges the instrument (Run Startup mode) and sends a message to enter Run Read Reagent mode (effectively skipping Run Access mode, where there was no work to do).

3. From Running mode, the last active sample completes and the remote software transitions itself to Run Access mode.

4. After a Landing Zone has been achieved, the remote software transitions itself to Run Paused Access mode. This mode is more restricted in what the user can do (no sample drawers may be opened, but reagents can be changed/replenished).

Both the host and the instrument are able to change the instrument states. It is indicated both in text and on the logic diagram when the either host or instrument has the responsibility to make the state transition (see FIG. 19).

Timers

Each timer is configurable. At initialization time, the Host sends the values of these timers down to the instrument. The values are stored in an ARGUMENTS table of the host software.

These timers are:
Sample Drawer Loaded timeout, for example, set to 30 seconds.
Reagent Hood Opened timeout, for example, set to 2 seconds.
Flags
The flags include:
Cover Lid Flag (specifically, "CoverLidWasLifted")
   This flag indicates that the contents of the reagent carousel have been modified by the user since the last time the barcodes were scanned.
   Flag is cleared (false) when the reagent scans begin.
   Flag is set (true) when the reagent door has been opened.

Flag is set (true) if the host is unable to qualify all reagents and the user must take corrective action.

Flag is used to determine whether to re-read reagents when the host sets the mode to "Run Read Reagent Mode".

Flag (when set) is used to NAK the 2 host messages that set the reagent ID data.

As a rule, any state transition out of Run Read Reagent mode that is not into Run Starting, Run Resuming or Run Read Samples mode will also clear the Flag. This covers the reagent barcode reading failure cases.

Cover Lid Current State

This flag indicates the current state of the reagent cover/door, open or closed.

The event of changing the state also causes a mode change to "Run Access Mode", if reading barcodes.

Landing Zone Flag

This flag indicates that the instrument is operating in a Landing Zone.

Flag is set when the "Run Pausing Mode" transitions to "Run Paused Access Mode"

Flag is cleared when "Run Resuming Mode" transitions to "Running Mode"

Run Access Mode

The instrument enters this mode either when all samples have completed, or an error has occurred during the processes leading up to starting runs. Opening the reagent hood when unlocked (during the barcode reading modes) will change the instrument back to one of the Run Access modes (there are 2!). Also, a reagent read failure, sample read failure, or run compile failure leads to the host changing the instrument mode back to Run Access. There, the user can either unload samples, change reagents, or fix the run compile problem at the host. The host will then send another mode change command to enter Run Read Reagent Mode.

During the Run Access Mode, the reagent hood and sample chambers are accessible. A timer is created for monitoring the hood switch and sample chamber activity. The timer begins a countdown to move to the next mode within the state machine. The timer is deactivated while the reagent hood is open. Once the reagent hood is closed, the timer resets and starts the countdown. Each time a sample drawer is opened, the timer resets and countdown is re-started. The timer also is deactivated when there are no samples in the ssLoaded state.

To exit the mode, a Set Operational Mode command is sent as a result of user action correcting an error at the host (such as reagent registration, sample barcode, or protocol).

The mode change will be NAK'd (not acknowledged) if the reagent hood is open.

Run Paused Access Mode

This mode is like Run Access mode, except sample access is prohibited. This is the Run Access mode used for Landing Zones. The instrument enters this mode from a successful Run Pausing mode, where the user may then open the reagent hood to shuffle/load/unload reagents as desired. A flag is set to indicate that this is a Landing Zone, in the transition from Run Pausing mode into Run Paused Access Mode. Here:

The host may send the Resume command to exit the mode.

Resume command may specify reagent product/serial/priming data and relocation information, but it will be ignored.

Run Read Reagent mode will be entered with knowledge of whether the reagents need scanning or not (the Cover Lid Flag).

The Resume will be NAK'd if the reagent hood is open.

Sample Loading During Idle or Access Mode

In cases where the user starts in Idle or Access mode, it can affect the path through the state machine if samples are loaded before reaching Run Access mode. In Idle mode, the user may press the "Running" button on the PC to get the instrument to Run Startup (via host message), then to Run Access mode (the instrument transitions itself). The sample states are all set to ssEmpty, since the predominant assumption is that the user only unloaded samples.

If the instrument is in Idle mode and has sufficient pressure to open/close sample drawers, the user will unload and might also load samples before pressing the Running button. If this occurs, the instrument could remain in Run Access mode, unaware that samples are loaded and no timers are running yet, thus only opening and closing a sample drawer(cell) will prod the instrument into action. This one sample will start running. Any other samples loaded when it was Idle will be detected automatically and started, once the instrument is processing samples normally in imRunning mode.

In Access mode, the instrument is pressurized and samples can be loaded/unloaded more easily. The loaded sample positions cannot be determined yet, so all the sample states are changed to ssLoaded automatically when the user presses the "Running" button on the PC. The instrument will go to Run Startup (via host message), then it will skip Run Access mode and go right into Run Read Reagent Mode. All the sample positions are detected and read once Run Read Sample mode is reached.

Also, if the user has opened any sample drawers in either of these modes and left them open, then presses the Running button, the user will be prompted to close the sample drawers first.

Run Read Reagent Mode

The instrument enters this mode from either Run Startup mode, Run Access mode, or Run Paused Access mode.

The Cover Lid State must be closed to enter this mode.

The Cover Lid Solenoid is not locked in this mode.

If the Cover Lid Flag is cleared (false) when the mode is entered, reagent reading is skipped.

If the Cover Lid Flag is set (true) when the mode is entered, a full reagent read is performed.

The Cover Lid Flag is cleared upon entry to this mode.

The Cover Lid Flag is set if the host determines there is a read failure or invalid barcode.

Sample drawers are accessible in this mode. A sample drawer opened and closed will transition to ssLoaded state.

The reagent barcode read process then consists of:

Nozzle Plate seeks to the "instrument center" position.

Home the reagent carousel.

Read the reagent barcodes starting from position 1 through position 35.

The remote software will store the data from each reagent barcode read.

The host software will request the reagent barcode data to be returned to the host application through a host command, with appropriate response.

The host application will qualify the reagents loaded on the reagent carousel based on:

Product is registered in the database.

Correct instrument type.

Valid expiration date.

Active reagent status.

If the reagent read occurs in a Landing Zone sequence, the reagents can be further qualified to know:

If the positioning on the carousel is valid (certain reagents are required to be side-by-side).

If sufficient tests remain to complete the staining runs.

If the user opens the hood during the read of reagents, the read will stop and the instrument transitions itself back to Run Access mode.

Once the reagent read is completed (either by doing a full read or skipping it) the remote stays in the Run Reagent Read mode, sets the submode to "Reagent Read Done", then waits. Then, if the Landing Zone flag is not set:
If reagent data is valid,
Reagent identifiers are downloaded by the host.
The host will send a mode change message to go to Run Read Sample mode.
Once the change to Run Read Sample mode is reached, the cover lid solenoid is locked.
If the reagent data is not valid,
The host will send a mode change message to go to Run Access Mode.
The Cover Lid Flag is set.
If the cover lid is opened at any time in this mode,
Reagent reads are stopped.
The Cover Lid Flag is set.
The mode is changed back to Run Access mode.
OR if the Landing Zone flag is set:
If a Resume message is sent while the door is still open, it will be NAK'd.
If reagent data is valid,
The host will send a Resume message, which must specify reagent product/serial/priming data and relocation information.
The Resume command will cause a transition to Run Resuming Mode.
Once the change to Run Resuming Mode is reached, the cover lid solenoid is locked.
If the reagent data is not valid,
The host will send a mode change message to go to Run Paused Access Mode.
The Cover Lid Flag is set.
If the cover lid is opened at any time in this mode,
Reagent reads are stopped.
The Cover Lid Flag is set.
The mode is changed to Run Paused Access mode.

Run Read Sample Mode

The instrument enters this mode from Run Read Reagent mode, and the Cover Lid solenoid is locked when the instrument is in this mode.

The remote software is placed in this mode by the host for a non-Landing Zone sequence. The remote software checks the sample states to determine if there is a need to read the sample barcodes in a specific position (ssLoaded state).

If any sample is in the ssLoaded state, the following steps will occur to read the samples:
Sample drawer opening is inhibited in this mode.
Home the nozzle plate.
Advance the Sample Detect station to the first sample needing inspection.
Detect the sample presence.
Depending on which is closer, move the Sample Detect station to the next sample needing inspection, OR move the Barcode Reader station to the next sample that was successfully detected.
Repeat until all samples in the ssLoaded state are both detected and scanned by the barcode reader (if present).
The remote software will store the data from each sample barcode read.
The host software will request the sample barcode data to be returned to the host application through a host command with appropriate response.
The host application will qualify the protocol assigned to the case sample based on
Protocol or Keycode is in the database.
Correct instrument type.
Protocol steps matching staining procedure steps.
The necessary reagents needed to perform the staining procedure are loaded on the reagent carousel.
If the previous reagent read was NOT for a Landing Zone sequence, the reagents can now be qualified to know:
If the positioning on the carousel is valid (certain reagents are required to be side-by-side).
If sufficient tests remain to complete the staining runs.
If the user opens the hood during the read of samples, the read will stop and the instrument transitions itself back to Run Access mode.

Once the sample reading is completed for 0 or more samples, the remote stays in the Run Sample Read mode, and sets the submode to "Sample Read Done".
If the data is valid, the host will send a mode change messages to go to Run Starting Mode.
If the data is not valid, the host will send a mode change message to go to Run Access Mode.

Run Starting Mode

In this mode, the host application compiles and downloads the macro steps for each sample position to the remote. When the first staining run download is complete (there will be one for each sample, arriving serially), the remote software transitions automatically to Running mode.

Running Mode

Samples (such as on samples) are processed in lock step during the Running Mode. Any samples added during this mode are detected in lock step with the samples being processed. The sample will be detected and then read as the nozzle plate continues stepping. The host application will:
Request the barcode data.
Qualify the protocol.
Qualify the reagents are available with sufficient tests, and are ordered correctly on the carousel (the side-by-side requirement).
Compile the macro steps.
Download the macros to the remote software.
Start the staining process for the samples that were added. This activity happens without impacting the staining process on currently running samples.

Run Pausing Mode

The instrument will enter this mode from Running mode.
A Resume command will be sent here when the user decides not to pause the instrument, and to go back to running mode.
Resume command may specify reagent product/serial/priming data and relocation information, but it will be ignored.
Any sample positions already paused will be re-started.
Running mode will then be entered.

Completed Samples

When all the samples have completed the staining process, the remote software will transition itself back to Run Access Mode. While in this mode, the reagent hood will be unlocked and accessible for adding/removing reagents.

As described earlier in the Run Access mode, the internal timer for sample drawer access will be deactivated until a sample drawer is opened and closed to put a sample into the ssLoaded state. Once the sample drawer is closed the internal timer begins counting down. Each subsequent sample drawer opening and closing resets the timer. Once the timer has exhausted and the reagent hood is in the closed position, the nozzle plate is homed and begins the sample detection process, and then continues through the state machine again to the Running mode.

Example 5

Landing Zones—Embedded Software Design Considerations

Landing Zone Parameters:

A number of configurable parameters are provided in order to accurately accommodate the computation of landing zones, some of which parameters are illustrated in FIG. 20.
Total Allotted Landing Zone Timeout The maximum number of seconds any one sample can remain in a Paused state. This includes, the time it takes for all processing sample positions to come to the pause point, the time required by the user to switch out the desired dispensers along with the time for the instrument to rescan all the reagent barcodes.

The instrument will sound a major alarm Hood Warning Timeout seconds before this timeout is reached.

Each sample is separately timed from when it was actually paused.

Once this timeout has expired for a sample, the instrument will raise a sample level exception that will be logged on the sample's run report.

The software defaults to four hours (14,400 seconds)

Configurable via a Host Option Argument (Data Type 23)

Landing Zone Maximum Secs

Hood Warning Timeout

This value represents the optimal amount of time it would take an operator to exchange 80% of the dispensers from the reagent carousel.

Once the reagent hood has been opened, by the user during a Landing Zone, this timeout is used to drive a minor error "snooze" alarm.

When the hood is kept open for longer than this timeout value, the instrument will alarm with a minor error fault.

Once the hood is closed the alarm is silenced.

If the hood is reopened, the process is repeated until Total Allotted Landing Zone Timeout is reached.

Defaulting to ten minutes (600 seconds)

Configurable via a Host Option Argument (Data Type 23)

Landing Zone Hood Warning Secs

Auto Resume Timeout

The amount of time the instrument will wait, after all samples have been paused and the reagent hood remains unopened, before automatically resuming with sample processing.

Defaulting to ten minutes (600 seconds)

Configurable via a Host Option Argument (Data Type 23)

Landing Zone Auto Resume Secs

Manual Resume Timeout

The amount of time the instrument will wait, after the reagent hood is closed during a Landing Zone, before automatically advance into a Run Reading Reagents mode and begin scanning reagent barcodes.

Defaulting to two seconds (2 seconds)

Hard coded in the remote staining module firmware.

Landing Zones Algorithms:

Computing accurate landing zones depends on computing accurate run times.

Once establishing how long each individual procedure step of each staining protocol currently processing on the instrument will take to execute, the time between pause points can be determined.

Provided with the protocol and the starting time of each sample run identify the first set of available pause points to establish a valid landing zone. Once the first landing zone has been determined, repeat the process establishing successive landing zones until all pause points from all samples have been depleted.

Some pause points from some samples may be overlooked to optimize sample processing throughput and to prevent tissue damage by not violating the maximum pause time but still providing ample down time for a user to switch out the required reagent dispensers and to rescan the barcodes.

Rules and Considerations:

After the instrument has been instructed to pause and while it is in the process of pausing execution of each sample's staining, the user has the opportunity to cancel the landing zone instruction and resume.

The instrument is provided with up to Total Allotted Landing Zone Timeout minus 2 times the Hood Warning Timeout to reach the designated pause points.

The user has the option to cancel the selected landing zone while the instrument is pausing.

If the landing zone is canceled, but the samples have not yet reached their pause points, the landing zone remains as an option after it is canceled. However if any one of the samples reaches a designated pause point before the landing zone was canceled, such a paused samples resumes processing and that particular landing zone becomes no longer be available to the user.

Once all samples have been paused, the instrument will automatically resume on paused samples after waiting Auto Resume Timeout if the reagent hood seal is not broken by the user.

After the user opens the reagent hood, an alarm will sound after Hood Warning Timeout seconds have passed, to warn the user to close the reagent hood.

If the Total Allotted Landing Zone Timeout has expired, each sample that has been sitting for more than the allotted time window will receive an error in the run report to the following effect:

12-65: Landing Zone left unattended. Sample exceeded allotted pause time.

After the user addresses dispenser inventories needs and closes the reagent hood for Manual Resume Timeout seconds, the instrument will automatically start reading the reagent barcodes.

While the instrument is reading reagent barcodes, the user can re-open the reagent hood to return the instrument back to the landing zone.

All reagents currently "In Use" by paused samples are required to be on the reagent carousel, although some rearranging is allowed.

Once the new dispenser positioning information is downloaded to the instrument, unprimed dispensers are primed and execution is allowed to resume on all paused samples.

If required dispensers are found to be missing from the reagent carousel or any other dispenser related infractions are encountered, the instrument will sound the landing zone alarm and the instrument remains in the landing zone.

Other dispenser related infractions:

Product not registered

Product expired

Product exhausted

Product not registered

Product missing from Argument table

Required kit component missing
Dispensers must be beside each other
Reagent Pick List:
After a Landing Zone has been selected by the user, a Reagent Pick List is available to provide a list of reagents to add or remove from the instrument during the selected landing zone.

The report can include the reagent name, product type, product code and test needed required to process all samples currently in a compiler failed state (i.e. samples that have not been able to start because the reagents they require were not on the instrument) that have a valid protocol.

The report also can include all dispensers currently on the reagent carousel that are expired or exhausted, or no longer in use by a sample process. This report includes the position of the reagent carousel, reagent name, product type, expiration date and remaining test count of each dispenser that should be removed from the instrument at the selected landing zone.

Example 6

Graphical User Interface

Figure 21:
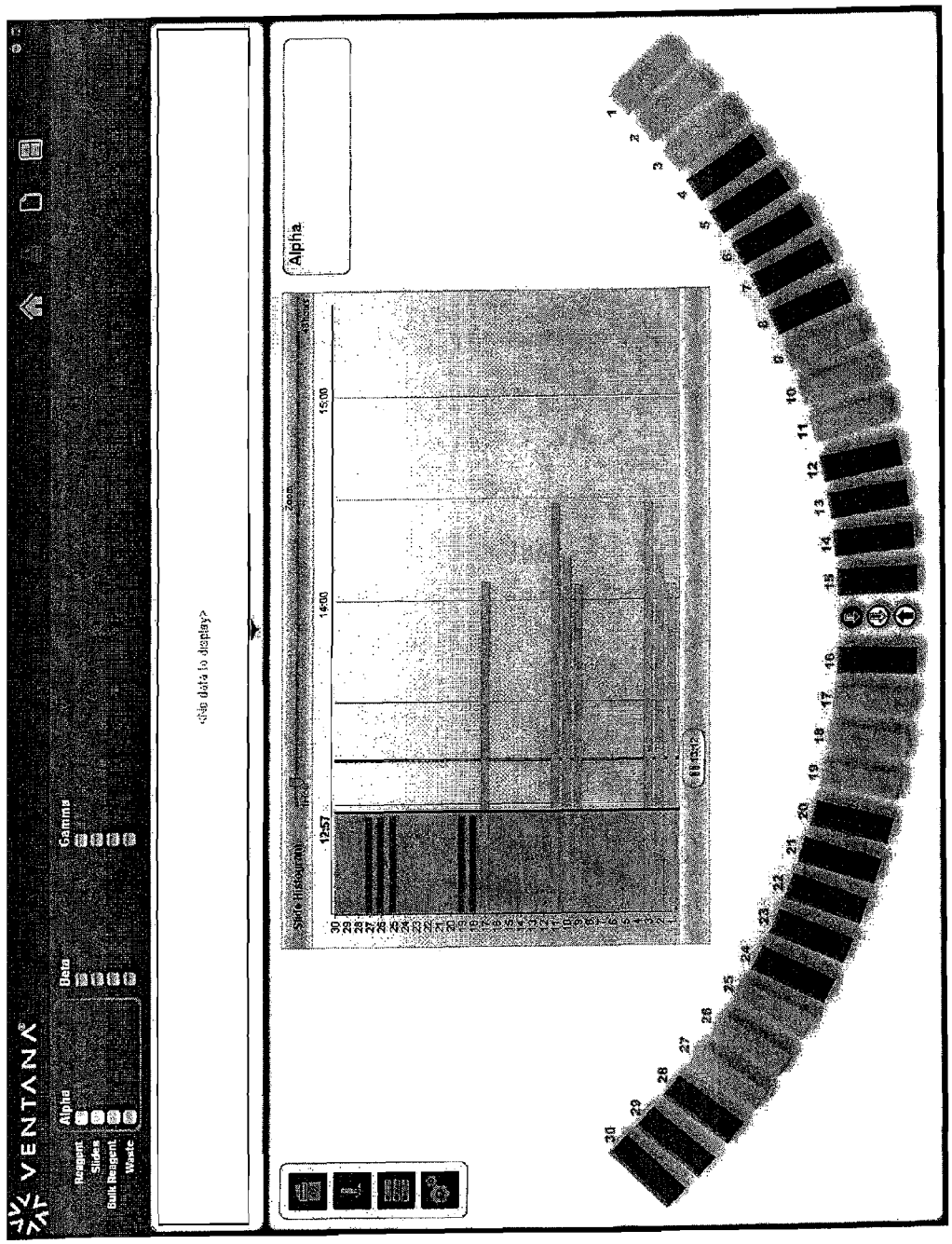
FIG. 21 shows an example of an embodiment of an instrument screen shot of the graphical user interface display that conveys important information to a user.
Figure 22:
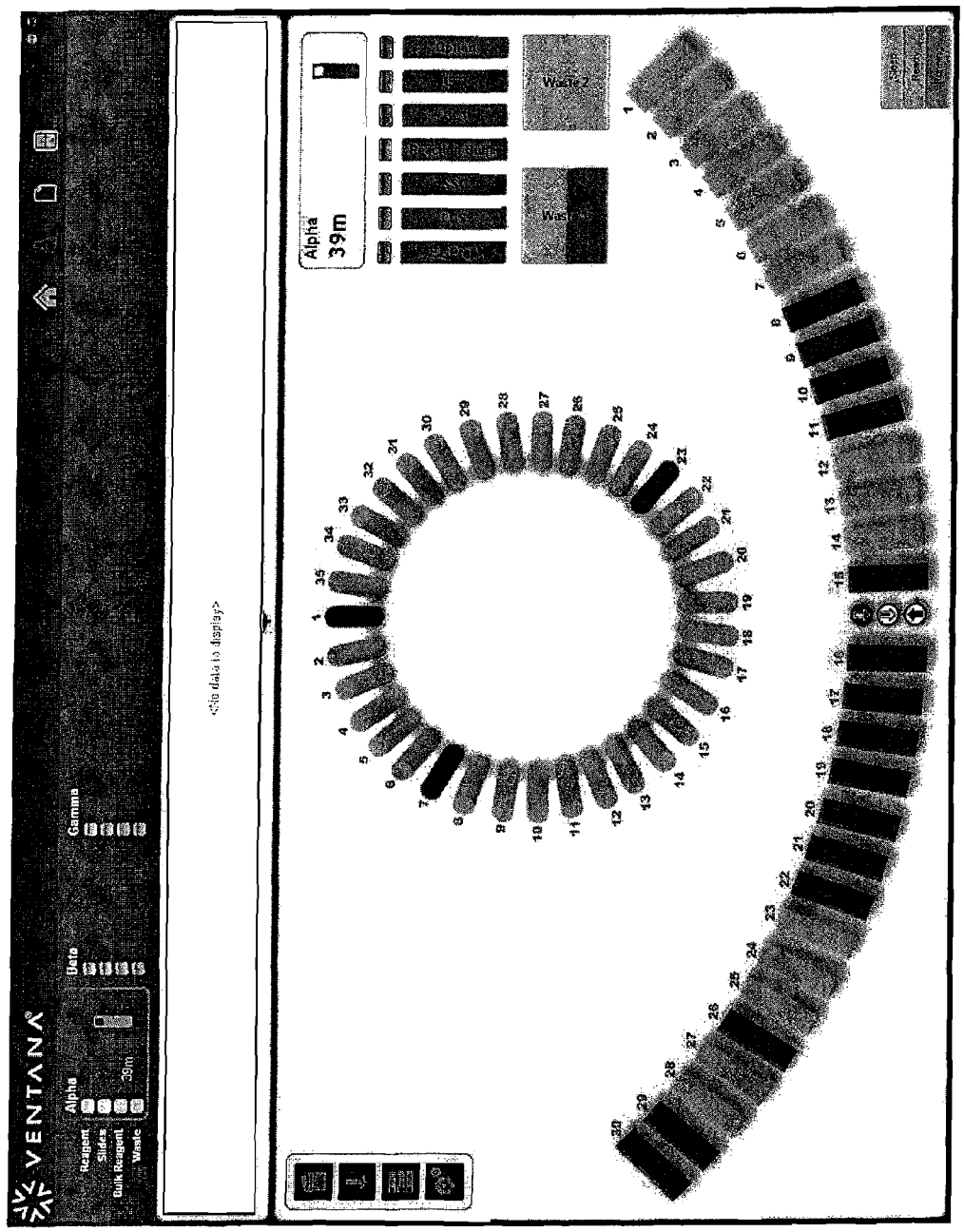
FIG. 22 shows an example of an embodiment of an instrument screen shot of the graphical user interface display that conveys important information to a user.

Shown in FIGS. 21 and 22 are examples of screen shots of graphical user interface displays that conveys important information to a user. In FIG. 21, the bar-graph in the center of the display conveys the progress of each of several samples that are being processed simultaneously. Occupied sample cells are noted in the arc of numbered positions, and the relative progress of each of the samples in those cells are indicated the bar graph in the center.

In FIG. 22, the display shows both the status of the sample cells as well as the status of reagents held in a reagent carousel, and the levels of bulk fluids (such as cell-conditioning fluids, buffers, rinse solutions, mineral oil (used to create a "coverslip" over an aqueous liquid placed on a samples held on a substrate). Also displayed is the level of waste in the waste containers. All of these features displayed in the graphical user interface permit real-time monitoring of sample processing, and help alert users to conditions that are preventing samples from being processed further.

Despite having described illustrative embodiments in detail, it should be understood that the disclosed invention is not limited to the particular embodiments described in the specification and that many changes may be made without departing from the true scope and spirit of the invention, which is defined by the claims that follow. For example, other configurations of independently movable substrate support units that allow continuous or near continuous addition and retrieval of samples from the disclosed apparatus are contemplated, such as tower structures having stacks of substrate support units accessed by a sample processor in a vertical grid or a vertical arc, and linear configurations where the substrate support units are in a line and processed using a substrate processor that moves in a parallel path to the line of the substrate support units. Furthermore, those skilled in the art to which the invention pertains will recognize, or be able to ascertain through no more than routine experimentation, many equivalents to the embodiments described herein. Such equivalents are intended to fall within the scope of the claims.

We claim:

1. A method for continuous-access processing of a plurality of individual substrate-supported biological samples in an automated biological processing apparatus, the apparatus having a plurality of individual and separate substrate support units arranged adjacent to each other in substantially the same plane along a minor arc of a circle and where each of the individual substrate support units are automatedly and independently movable between a separate processing position and a separate access position, and an elongate nozzle plate rotatably mounted at the center of the circle and that extends toward the minor arc, but in a plane above the plurality of substrate holders, and along a radial line of the minor arc, wherein a cylindrical reagent dispenser carousel including at least one reagent dispenser is rotatably mounted on the top side of the elongate nozzle plate, the elongate nozzle plate having at least one device and at least one nozzle mounted to the underside of the nozzle plate, the at least one nozzle being in fluid communication with the reagent dispenser on the reagent dispenser carousel; the cylindrical reagent dispenser carousel having an axis and a second radius, the second radius being smaller than the first radius such that the at least one reagent dispenser on the carousel can be positioned over a substrate holder along the minor arc through a combination of rotational movement of the elongate nozzle plate around the center of the circle and rotational movement of the cylindrical reagent dispenser carousel around its axis, the method comprising:

placing a substrate-supported sample onto an unoccupied substrate support unit in an access position;
automatedly moving an individual substrate support unit and its substrate-supported sample to a processing position in response to a user command;
automatedly detecting the substrate-supported sample moved into the processing position on the substrate support unit;
automatedly qualifying one or more reagents on the cylindrical reagent carousel rotatably mounted on said elongate nozzle plate and needed to perform a staining procedure; and
automatedly initiating processing of the detected sample in a pre-determined order of steps, the pre-determined order of steps carried out on the sample independently of processing steps in progress on other samples already being processed by the apparatus and independently of processing steps initiated for additional samples later added to the system wherein said nozzle plate sequentially moves the one or more different devices and one or more nozzles mounted to the underside of said nozzle plate above said substrate-supported samples to process one or more substrate-supported samples simultaneously.

2. The method of claim 1 further comprising automatedly alerting a user when processing of a sample is completed.

3. The method of claim 2 further comprising prompting a user to input a command causing the completed sample to be moved on the substrate support unit into the access position for retrieval of the completed sample from the apparatus.

4. The method of claim 3, wherein the command causing the completed sample to be moved to the access position for retrieval comprises a touch command executed through a sensor located on an exterior portion of the substrate support unit.

5. The method of claim 1, wherein a sample is a member of a pre-selected grouping of samples and further comprising automatedly alerting a user when processing of all the samples in the pre-selected grouping is completed.

6. The method of claim 5, wherein the pre-selected grouping of related samples includes two or more samples to be processed with a reagent selected from the group consisting of histochemical stains, immunochemical reagents, and in situ hybridization reagents.

7. The method of claim 5, wherein the pre-selected grouping of related samples comprises two or more samples obtained from the same subjects.

8. The method of claim 1, wherein initiating processing of the sample in the pre-determined order of steps comprises initiating processing according to an order of steps encoded by a machine-readable code associated with the substrate-supported sample.

9. The method of claim 1, wherein the separate processing position and the separate access position of each of the plurality of substrate support units lie along different radial lines of a minor arc of a circle.

10. The method of claim 1 further comprising alerting a user that a substrate support unit of the apparatus is unoccupied and ready to receive a substrate supported sample, or alerting the user that a substrate-supported sample for which processing is completed can be retrieved from the apparatus to provide the unoccupied substrate support unit.

11. The method of claim 1 wherein said processing of the detected sample further comprising automatedly positioning said cylindrical reagent dispenser carousel and a reagent dispenser contained thereon above a substrate-supported sample and automatedly dispensing a reagent from said reagent dispenser onto said substrate-supported sample.

12. The method of claim 1, wherein the step of qualifying one or more reagents on the cylindrical reagent dispenser carousel comprises determining automated biological processing apparatus.

13. The method of claim 1, wherein the step of qualifying one or more reagents on the cylindrical reagent dispenser carousel comprises determining whether sufficient reagent exists to complete a protocol.

14. The method of claim 1, wherein the step of qualifying one or more reagents on the cylindrical reagent dispenser carousel comprises determining the expiration date of the reagent.

15. The method of claim 1, wherein the user command comprises a touch command executed through a sensor located on an exterior portion of the substrate-support unit.

* * * * *